(12) United States Patent
Hass et al.

(10) Patent No.: US 7,776,573 B2
(45) Date of Patent: Aug. 17, 2010

(54) CRYSTAL STRUCTURE OF CRIG AND C3B:CRIG COMPLEX

(75) Inventors: Philip Hass, Moss Beach, CA (US); Jianping Yin, Foster City, CA (US); Kenneth Katschke, Millbrae, CA (US); Micah Steffek, Walnut Creek, CA (US); Menno Van Lookeren Campagne, San Francisco, CA (US); Christian Wiesmann, Brisbane, CA (US)

(73) Assignee: Genentech, Inc., South San Francisco, CA (US)

( * ) Notice: Subject to any disclaimer, the term of this patent is extended or adjusted under 35 U.S.C. 154(b) by 299 days.

(21) Appl. No.: 11/809,353

(22) Filed: May 30, 2007

(65) Prior Publication Data

US 2008/0045697 A1 Feb. 21, 2008

Related U.S. Application Data

(60) Provisional application No. 60/839,363, filed on Aug. 21, 2006, provisional application No. 60/806,225, filed on Aug. 3, 2006, provisional application No. 60/810,271, filed on Jun. 1, 2006.

(51) Int. Cl.
*C12N 9/00* (2006.01)
*G01N 31/00* (2006.01)

(52) U.S. Cl. .......................... 435/183; 436/4

(58) Field of Classification Search .................. None
See application file for complete search history.

(56) References Cited

FOREIGN PATENT DOCUMENTS

| WO | WO 99/40100 A1 | 8/1999 |
|---|---|---|
| WO | WO 99/46281 | 9/1999 |
| WO | WO 00/12703 A2 | 3/2000 |
| WO | WO 00/37638 A2 | 6/2000 |
| WO | WO 01/36432 A2 | 5/2001 |
| WO | WO 2006/042329 | 4/2006 |

OTHER PUBLICATIONS

McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Helmy, K. Y., et al., Cell, 124(5): 915-927 (2006).
Helmy, K.Y., et al., Cell, Online: http://www.sciendirect.com (2006).
Molina, H., et al., Journal of Immunology, 153(2): 789-795 (1994).
Wiesmann, C., et al., Nature, 444(7116): 217-220 (2006).
Blast Report, http://expasy.org/cgi-bin/niceprot.pl/printable?ac=Q80WA3.
Langnaese, et al., "Cloning of Z39Ig, a novel gene with immunoglobulin-like domains located on human chromosome X1", BBA, pp. 522-525, (2000).

* cited by examiner

*Primary Examiner*—Suzanne M. Noakes
(74) *Attorney, Agent, or Firm*—Bonny G. Yeung; Jeffery Bernhardt; Ginger R. Dreger

(57) ABSTRACT

The present invention concerns determination of the crystal structure of the macrophage specific receptor, CRIg (earlier referred to as STIgMA), and its complex with the C3b and C3c subunits of complement C3 (C3b:CRIg and C3c:CRIg complexes). The invention further concerns the use of the crystal structure of CRIg or the C3b:CRIg complex to screen for and identify molecules structurally and/or functionally related to CRIg, including CRIg agonists and antagonists.

4 Claims, 14 Drawing Sheets

(11 of 14 Drawing Sheet(s) Filed in Color)

A

B

C

D

SEQUENCE LISTING

```
<160> NUMBER OF SEQ ID NOS: 7

<210> SEQ ID NO 1
<211> LENGTH: 321
<212> TYPE: PRT
<213> ORGANISM: homo sapiens

<400> SEQUENCE: 1

Met Gly Ile Leu Leu Gly Leu Leu Leu Gly His Leu Thr Val Asp
1               5                   10                  15

Thr Tyr Gly Arg Pro Ile Leu Glu Val Pro Glu Ser Val Thr Gly Pro
                20                  25                  30

Trp Lys Gly Asp Val Asn Leu Pro Cys Thr Tyr Asp Pro Leu Gln Gly
            35                  40                  45

Tyr Thr Gln Val Leu Val Lys Trp Leu Val Gln Arg Gly Ser Asp Pro
        50                  55                  60

Val Thr Ile Phe Leu Arg Asp Ser Ser Gly Asp His Ile Gln Gln Ala
65                  70                  75                  80

Lys Tyr Gln Gly Arg Leu His Val Ser His Lys Val Pro Gly Asp Val
                85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys Leu Ser Val Ser Lys Pro Thr
```

-continued

```
                130                 135                 140
Val Thr Thr Gly Ser Gly Tyr Gly Phe Thr Val Pro Gln Gly Met Arg
145                 150                 155                 160

Ile Ser Leu Gln Cys Gln Ala Arg Gly Ser Pro Pro Ile Ser Tyr Ile
                165                 170                 175

Trp Tyr Lys Gln Gln Thr Asn Asn Gln Glu Pro Ile Lys Val Ala Thr
                180                 185                 190

Leu Ser Thr Leu Leu Phe Lys Pro Ala Val Ile Ala Asp Ser Gly Ser
                195                 200                 205

Tyr Phe Cys Thr Ala Lys Gly Gln Val Gly Ser Glu Gln His Ser Asp
210                 215                 220

Ile Val Lys Phe Val Val Lys Asp Ser Ser Lys Leu Leu Lys Thr Lys
225                 230                 235                 240

Thr Glu Ala Pro Thr Thr Met Thr Tyr Pro Leu Lys Ala Thr Ser Thr
                245                 250                 255

Val Lys Gln Ser Trp Asp Trp Thr Thr Asp Met Asp Gly Tyr Leu Gly
                260                 265                 270

Glu Thr Ser Ala Gly Pro Gly Lys Ser Leu Pro Val Phe Ala Ile Ile
                275                 280                 285

Leu Ile Ile Ser Leu Cys Cys Met Val Val Phe Thr Met Ala Tyr Ile
                290                 295                 300

Met Leu Cys Arg Lys Thr Ser Gln Gln Glu His Val Tyr Glu Ala Ala
305                 310                 315                 320

Arg
```

<210> SEQ ID NO 2
<211> LENGTH: 399
<212> TYPE: PRT
<213> ORGANISM: homo sapiens

<400> SEQUENCE: 2

```
Met Gly Ile Leu Leu Gly Leu Leu Leu Gly His Leu Thr Val Asp
  1               5                  10                  15

Thr Tyr Gly Arg Pro Ile Leu Glu Val Pro Glu Ser Val Thr Gly Pro
                 20                  25                  30

Trp Lys Gly Asp Val Asn Leu Pro Cys Thr Tyr Asp Pro Leu Gln Gly
                 35                  40                  45

Tyr Thr Gln Val Leu Val Lys Trp Leu Val Gln Arg Gly Ser Asp Pro
 50                  55                  60

Val Thr Ile Phe Leu Arg Asp Ser Ser Gly Asp His Ile Gln Gln Ala
 65                  70                  75                  80

Lys Tyr Gln Gly Arg Leu His Val Ser His Lys Val Pro Gly Asp Val
                 85                  90                  95

Ser Leu Gln Leu Ser Thr Leu Glu Met Asp Asp Arg Ser His Tyr Thr
                100                 105                 110

Cys Glu Val Thr Trp Gln Thr Pro Asp Gly Asn Gln Val Val Arg Asp
                115                 120                 125

Lys Ile Thr Glu Leu Arg Val Gln Lys Leu Ser Val Ser Lys Pro Thr
                130                 135                 140

Val Thr Thr Gly Ser Gly Tyr Gly Phe Thr Val Pro Gln Gly Met Arg
145                 150                 155                 160

Ile Ser Leu Gln Cys Gln Ala Arg Gly Ser Pro Pro Ile Ser Tyr Ile
                165                 170                 175

Trp Tyr Lys Gln Gln Thr Asn Asn Gln Glu Pro Ile Lys Val Ala Thr
```

-continued

```
                    180                 185                 190
Leu Ser Thr Leu Leu Phe Lys Pro Ala Val Ile Ala Asp Ser Gly Ser
        195                 200                 205

Tyr Phe Cys Thr Ala Lys Gly Gln Val Gly Ser Glu Gln His Ser Asp
        210                 215                 220

Ile Val Lys Phe Val Lys Asp Ser Ser Lys Leu Leu Lys Thr Lys
225                 230                 235                 240

Thr Glu Ala Pro Thr Thr Met Thr Tyr Pro Leu Lys Ala Thr Ser Thr
                    245                 250                 255

Val Lys Gln Ser Trp Asp Trp Thr Thr Asp Met Asp Gly Tyr Leu Gly
            260                 265                 270

Glu Thr Ser Ala Gly Pro Gly Lys Ser Leu Pro Val Phe Ala Ile Ile
        275                 280                 285

Leu Ile Ile Ser Leu Cys Cys Met Val Val Phe Thr Met Ala Tyr Ile
        290                 295                 300

Met Leu Cys Arg Lys Thr Ser Gln Gln Glu His Val Tyr Glu Ala Ala
305                 310                 315                 320

Arg Ala His Ala Arg Glu Ala Asn Asp Ser Gly Glu Thr Met Arg Val
                    325                 330                 335

Ala Ile Phe Ala Ser Gly Cys Ser Ser Asp Glu Pro Thr Ser Gln Asn
            340                 345                 350

Leu Gly Asn Asn Tyr Ser Asp Glu Pro Cys Ile Gly Gln Glu Tyr Gln
        355                 360                 365

Ile Ile Ala Gln Ile Asn Gly Asn Tyr Ala Arg Leu Leu Asp Thr Val
        370                 375                 380

Pro Leu Asp Tyr Glu Phe Leu Ala Thr Glu Gly Lys Ser Val Cys
385                 390                 395

<210> SEQ ID NO 3
<211> LENGTH: 305
<212> TYPE: PRT
<213> ORGANISM: homo sapiens

<400> SEQUENCE: 3

Met Gly Ile Leu Leu Gly Leu Leu Leu Gly His Leu Thr Val Asp
 1               5                  10                  15

Thr Tyr Gly Arg Pro Ile Leu Glu Val Pro Glu Ser Val Thr Gly Pro
            20                  25                  30

Trp Lys Gly Asp Val Asn Leu Pro Cys Thr Tyr Asp Pro Leu Gln Gly
        35                  40                  45

Tyr Thr Gln Val Leu Val Lys Trp Leu Val Arg Gly Ser Asp Pro
    50                  55                  60

Val Thr Ile Phe Leu Arg Asp Ser Ser Gly Asp His Ile Gln Gln Ala
65                  70                  75                  80

Lys Tyr Gln Gly Arg Leu His Val Ser His Lys Val Pro Gly Asp Val
                85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys His Ser Ser Lys Leu Leu Lys
    130                 135                 140

Thr Lys Thr Glu Ala Pro Thr Thr Met Thr Tyr Pro Leu Lys Ala Thr
145                 150                 155                 160
```

```
Ser Thr Val Lys Gln Ser Trp Asp Trp Thr Asp Met Asp Gly Tyr
            165                 170                 175

Leu Gly Glu Thr Ser Ala Gly Pro Gly Lys Ser Leu Pro Val Phe Ala
            180                 185                 190

Ile Ile Leu Ile Ile Ser Leu Cys Cys Met Val Val Phe Thr Met Ala
            195                 200                 205

Tyr Ile Met Leu Cys Arg Lys Thr Ser Gln Gln Glu His Val Tyr Glu
210                 215                 220

Ala Ala Arg Ala His Ala Arg Glu Ala Asn Asp Ser Gly Glu Thr Met
225                 230                 235                 240

Arg Val Ala Ile Phe Ala Ser Gly Cys Ser Ser Asp Glu Pro Thr Ser
                245                 250                 255

Gln Asn Leu Gly Asn Asn Tyr Ser Asp Glu Pro Cys Ile Gly Gln Glu
            260                 265                 270

Tyr Gln Ile Ile Ala Gln Ile Asn Gly Asn Tyr Ala Arg Leu Leu Asp
            275                 280                 285

Thr Val Pro Leu Asp Tyr Glu Phe Leu Ala Thr Glu Gly Lys Ser Val
            290                 295                 300

Cys
305

<210> SEQ ID NO 4
<211> LENGTH: 280
<212> TYPE: PRT
<213> ORGANISM: mus musculus

<400> SEQUENCE: 4

Met Glu Ile Ser Ser Gly Leu Leu Phe Leu Gly His Leu Ile Val Leu
1               5                   10                  15

Thr Tyr Gly His Pro Thr Leu Lys Thr Pro Glu Ser Val Thr Gly Thr
            20                  25                  30

Trp Lys Gly Asp Val Lys Ile Gln Cys Ile Tyr Asp Pro Leu Arg Gly
            35                  40                  45

Tyr Arg Gln Val Leu Val Lys Trp Leu Val Arg His Gly Ser Asp Ser
50                  55                  60

Val Thr Ile Phe Leu Arg Asp Ser Thr Gly Asp His Ile Gln Gln Ala
65                  70                  75                  80

Lys Tyr Arg Gly Arg Leu Lys Val Ser His Lys Val Pro Gly Asp Val
                85                  90                  95

Ser Leu Gln Ile Asn Thr Leu Gln Met Asp Asp Arg Asn His Tyr Thr
            100                 105                 110

Cys Glu Val Thr Trp Gln Thr Pro Asp Gly Asn Gln Val Ile Arg Asp
            115                 120                 125

Lys Ile Ile Glu Leu Arg Val Arg Lys Tyr Asn Pro Pro Arg Ile Asn
130                 135                 140

Thr Glu Ala Pro Thr Thr Leu His Ser Ser Leu Glu Ala Thr Thr Ile
145                 150                 155                 160

Met Ser Ser Thr Ser Asp Leu Thr Thr Asn Gly Thr Gly Lys Leu Glu
                165                 170                 175

Glu Thr Ile Ala Gly Ser Gly Arg Asn Leu Pro Ile Phe Ala Ile Ile
            180                 185                 190

Phe Ile Ile Ser Leu Cys Cys Ile Val Ala Val Thr Ile Pro Tyr Ile
            195                 200                 205

Leu Phe Arg Cys Arg Thr Phe Gln Gln Glu Tyr Val Tyr Gly Val Ser
            210                 215                 220
```

```
Arg Val Phe Ala Arg Lys Thr Ser Asn Ser Glu Glu Thr Thr Arg Val
225                 230                 235                 240

Thr Thr Ile Ala Thr Asp Glu Pro Asp Ser Gln Ala Leu Ile Ser Asp
            245                 250                 255

Tyr Ser Asp Asp Pro Cys Leu Ser Gln Glu Tyr Gln Ile Thr Ile Arg
            260                 265                 270

Ser Thr Met Ser Ile Pro Ala Cys
        275                 280

<210> SEQ ID NO 5
<211> LENGTH: 118
<212> TYPE: PRT
<213> ORGANISM: rattus rattus

<400> SEQUENCE: 5

His Pro Val Leu Lys Thr Pro Glu Arg Val Thr Gly Thr Trp Lys Gly
1               5                   10                  15

Asp Val Lys Ile Gln Cys Ile Tyr Asn Pro Leu Thr Gly Tyr Arg Glu
            20                  25                  30

Val Leu Val Lys Trp Leu Val Gln Arg Gly Ser Asp His Val Thr Ile
        35                  40                  45

Phe Leu Arg Asp Tyr Ser Gly Asp His Val Gln Gln Ala Lys Tyr Arg
    50                  55                  60

Gly Arg Leu Lys Val Ser His Lys Val Pro Gly Asp Val Ser Leu Gln
65                  70                  75                  80

Leu Asn Asn Leu Gln Met Asp Asp Arg Asn His Tyr Thr Cys Glu Val
                85                  90                  95

Thr Trp Gln Thr Pro Asp Gly Asp Gln Val Arg Arg Asp Lys Ile Thr
            100                 105                 110

Glu Leu Arg Val Gln Lys
        115

<210> SEQ ID NO 6
<211> LENGTH: 118
<212> TYPE: PRT
<213> ORGANISM: bos taurus

<400> SEQUENCE: 6

His Pro Ile Leu Glu Val Pro Glu Ser Val Thr Gly Pro Trp Lys Gly
1               5                   10                  15

Asp Val Asn Ile Pro Cys Thr Tyr Gly Pro Leu Gln Gly Tyr Thr Gln
            20                  25                  30

Val Leu Val Lys Trp Leu Val Glu Arg Gly Ser Asp Ser Val Thr Ile
        35                  40                  45

Phe Leu Arg Asp Pro Ser Gly Asp His Ile Gln Gln Ala Lys Tyr Arg
    50                  55                  60

Gly Arg Leu Lys Val Ser His Lys Val Pro Gly Asp Val Ser Leu Gln
65                  70                  75                  80

Ile Asn Thr Leu Gln Met Asp Asp Arg Ser His Tyr Thr Cys Glu Val
                85                  90                  95

Thr Trp Gln Thr Pro Asp Gly Asn Gln Val Val Arg Asp Lys Ile Val
            100                 105                 110

Glu Leu Arg Val Gln Lys
        115

<210> SEQ ID NO 7
```

```
<211> LENGTH: 118
<212> TYPE: PRT
<213> ORGANISM: macaca

<400> SEQUENCE: 7

Arg Pro Ile Leu Glu Val Pro Glu Ser Ile Thr Gly Pro Trp Lys Gly
 1               5                  10                  15

Asp Val Asn Ile Pro Cys Thr Tyr Gly Pro Leu Gln Gly Tyr Thr Gln
             20                  25                  30

Val Leu Val Lys Trp Leu Val Gln Arg Gly Ser Asp Pro Val Thr Ile
         35                  40                  45

Phe Leu Arg Asp Ser Ser Gly Asp His Ile Gln Gln Ala Lys Tyr Gln
     50                  55                  60

Gly Arg Leu His Val Asn Gln Lys Val Pro Gly Asp Val Ser Leu Gln
 65                  70                  75                  80

Leu Ser Thr Leu Glu Met Asp Asp Gln Ser His Tyr Thr Cys Glu Val
             85                  90                  95

Thr Trp Gln Thr Pro Asp Gly Asn Gln Val Val Arg Asp Lys Ile Thr
            100                 105                 110

Glu Leu Arg Val Gln Lys
            115
```

CRYSTAL STRUCTURE OF CRIG AND C3B:CRIG COMPLEX

CROSS-REFERENCE TO RELATED APPLICATIONS

This application claims priority under Section 119(e) and the benefit of U.S. Provisional Application Ser. Nos. 60/839,363, filed Aug. 21, 2006, 60/806,225, filed Aug. 3, 2006 and 60/810,271, filed Jun. 1, 2006, the entire disclosures of which are incorporated herein in their entirety.

BACKGROUND OF THE INVENTION

1. Field of the Invention

The present invention concerns determination of the crystal structure of the macrophage specific receptor, CRIg (earlier referred to as STIGMA), and its complex with the C3b and C3c subunits of complement C3 (C3b:CRIg and C3c:CRIg complexes). The invention further concerns the use of the crystal structure of CRIg or the C3b:CRIg complex to screen for and identify molecules structurally and/or functionally related to CRIg, including CRIg agonists and antagonists.

2. Description of the Related Art

The complement system is a complex enzyme cascade made up of a series of serum glycoproteins, that normally exist in inactive, pro-enzyme form. C3 plays a key role in complement activation as it represents the convergence point of the three main pathways, the classical, lectin and the alternative pathways of complement. C3 interacts with more than 20 proteins (M. J. Walport, N Engl J Med 344, 1058 (2001) and (M. J. Walport, N Engl J Med 344, 1140 (2001)) via a number of distinct binding sites that are only exposed after its cleavage by the proteolytic enzyme C3 convertase (J. Janssen et al., Nature 437, 505 (2005)). The first proteolytic cleavage step generates the small (9 kDa) C3a peptide, also called anaphylatoxin, and the large (177 kDa) C3b fragment. Cleavage of C3 to C3a and C3b induces conformational changes which expose a buried thio-ester bond in C3b that can now covalently attach the molecule to particle surfaces. This process, termed "opsonization", targets the particles for binding to macrophage complement receptors that will then clear the particle from the system.

Recently, CRIg has been identified as a receptor for C3b/iC3b opsonized particles (K. Y. Helmy et al., Cell 124, 915 (2006)). CRIg binds C3b, iC3b, as well as C3c, but is unable to form a complex with the inactive precursor C3.

In addition to its function as an opsonin, C3b is a subunit of the C3 and C5 convertases of complement. C3b first binds to the serine protease factor B (W. Vogt, G. Schmidt, B. Von Buttlar, L. Dieminger, Immunology 34, 29 (1978); Z. Fishelson, M. K. Pangburn, H. J. Muller-Eberhard, J Biol Chem 258, 7411 (1983)). This complex, after recruitment of and activation by factor D, then forms the C3bBb complex, the active C3 convertase of the alternative pathway (AP). Addition of a second C3b molecule to the C3 convertase will result in the formation of $(C3b)_2Bb$, the C5 convertase of the alternative pathway of complement which has been shown to play a critical role in mediating inflammation in experimental animal models and human autoimmune and inflammatory diseases (M. J. Walport, K. A. Davies, B. J. Morley, M. Botto, Ann NY Acad Sci 815, 267 (1997)). The C3b subunits of the alternative pathway convertases serve as docking sites for the respective substrate C3 or C5 and are required for catalytic activity of the convertase (N. Rawal, M. K. Pangburn, J Immunol 164, 1379 (2000). The alternative pathway of complement amplifies complement activation initiated through any of the three pathways, the alternative, classical and mannose-binding lecting pathway. As a result, deficiencies in complement factor H, a regulator of the alternative pathway, result in amplification of inflammation (N. Rougier et al., J Am Soc Nephrol 9, 2318 (1998); M. A. Abrera-Abeleda et al., J Med Genet (Nov. 18, 2005)). Thus, cleavage of C3 and C5 by the alternative pathway complement convertases leads to opsonization, convertase generation and inflammation.

As a central component of the convertases, C3b serves as a target for numerous complement regulators. Among these are complement receptor 1 (CR1), membrane cofactor protein (MCP), decay accelerating factor (DAF), complement related receptor y (Crry), factor H and factor I (D. Hourcade, V. M. Holers, J. P. Atkinson, Adv Immunol 45, 381 (1989)). Binding of factor I leads to inactivation of C3b via proteolysis to form C3b and C3f (2 kDa) and finally the generation of C3dg (40 kDa), which contains the thio-ester domain (TED) and remains attached to the target, and C3c (135 kDa). A recent report on the crystal structures of C3 and C3c has significantly enhanced our understanding of the mechanism by which C3 is activated (B. J. Janssen et al., 2005, supra). C3c shows marked structural changes in comparison with C3 reflecting the consequences of multiple proteolytic cleavage steps. These structural studies suggested conformation-dependent mechanisms of C3-activation and -regulation, but do not provide an answer to the conformation of the activate species C3b.

SUMMARY OF THE INVENTION

The instant disclosure presents the crystal structure of the macrophage complement receptor CRIg, which is required for clearance of pathogens. In addition, the crystal structure of C3b and C3c in complex with CRIg is provided. This first structure of a convertase subunit in complex with a native cellular receptor and regulator of complement activation improves our understanding of the mechanism of complement activation and regulation. The invention also provides information about the C3b binding region of CRIg, and the domains and sequences within C3b participating in such binding, which can be used to identify molecules functionally related to CRIg, including CRIg agonists and antagonists.

In one aspect the invention concerns a crystal formed by a native sequence CRIg polypeptide or a functional fragment or conservative amino acid substitution variant thereof.

In one embodiment, the crystal has approximately the following cell constants a=30.3 Å, b=50.8 Å, c=62.0 Å, and a space group of $P2_12_12_1$.

In another embodiment, the native sequence CRIg polypeptide is selected from the group consisting of human CRIg polypeptides of SEQ ID NO: 1, 2, and 3; mouse CRIg polypeptide of SEQ ID NO: 4; rat CRIg polypeptide of SEQ ID NO: 5; bovine CRIg polypeptide of SEQ ID NO: 6; and monkey CRIg polypeptide of SEQ ID NO 7.

In yet another embodiment, the functional fragment of the CRIg polypeptide is an extracellular domain (ECD) sequence of a native sequence CRIg.

In a further embodiment, the crystal diffracts X-rays for the determination of atomic coordinates to a resolution of between about 1 and 40 Å, or to a resolution of at least about 5 Å, or at least about 4 Å, or at least about 3 Å.

In a still further embodiment, the invention concerns a CRIg crystal with the structural coordinates shown in Appendix 1.

In another aspect, the invention concerns a composition comprising a crystal as defined above.

In yet another aspect, the invention concerns a crystalline form of a complex between a native sequence CRIg polypeptides or a functional derivative or conservative amino acid substitution variant thereof, and complement factor C3b.

In one embodiment, the crystalline form of the complex has approximately the following cell constants a=97.6 Å; b=255.7 Å, c=180.3 Å, and a space group of C222$_1$.

In another embodiment, the crystalline form of the complex comprises one of human CRIg polypeptides of SEQ ID NO: 1, 2, and 3; mouse CRIg polypeptide of SEQ ID NO: 4; rat CRIg polypeptide of SEQ ID NO: 5; bovine CRIg polypeptide of SEQ ID NO: 6; and monkey CRIg polypeptide of SEQ ID NO 7.

In a further embodiment, the functional CRIg fragment is an extracellular domain (ECD) sequence of a native sequence CRIg.

In a still further embodiment, the crystalline form of the complex diffracts X-rays for the determination of atomic coordinates to a resolution of between about 1 and 40 Å, or to a resolution of at least about 5 Å, or at least about 4 Å, or at least about 3 Å.

In yet another embodiment, the crystalline form of the crystalline form of the CRIg:C3b complex has the structural coordinates shown in Appendix 2.

In further aspect, the invention concerns a crystalline form of a complex between a native sequence CRIg polypeptides or a functional derivative or conservative amino acid substitution variant thereof, and complement factor C3c.

In a particular embodiment, the crystalline form of the CRIg:C3c complex has approximately the following cell constants a=382.8 Å, b=65.0 Å, c=147.2 Å, β=102.7, and a space group of C2.

In another embodiment, the native sequence CRIg polypeptide present in the CRIg:C3C complex is selected from the group consisting of human CRIg polypeptides of SEQ ID NO: 1, 2, and 3; mouse CRIg polypeptide of SEQ ID NO: 4; rat CRIg polypeptide of SEQ ID NO: 5; bovine CRIg polypeptide of SEQ ID NO: 6; and monkey CRIg polypeptide of SEQ ID NO 7.

In yet another embodiment, the CRIg functional fragment present in the complex is an extracellular domain (ECD) sequence of a native sequence CRIg.

In a further embodiment, the crystalline form of the CRIg:C3c complex diffracts X-rays for the determination of atomic coordinates to a resolution of between about 1 and 40 Å, or to a resolution of at least about 5 Å, or at least about 4 Å, or at least about 3 Å.

In a particular embodiment, the CRIg:C3c complex has the structural coordinates shown in Appendix 3.

In a further aspect, the invention concerns a molecule or molecular complex comprising at least a portion of the C3b binding site of a CRIg polypeptide of SEQ ID NO: 2, or conservative substitutions thereof, wherein the binding site comprises at least one amino acid residue selected from the group consisting of 8, 14-15, 41-42, 44, 45-47, 50, 52, 54-61, 62, 64, 85-87, 89, 95, 99, 105, 107-110, and 111, and wherein the binding site is defined by a set of points having a distance of less than 4.7 Å from points representing atoms of the amino acids as represented by the structure coordinates listed in Appendix 2.

In another aspect, the invention concerns a three-dimensional configuration of points wherein at least a portion of the points are derived from structure coordinates of Appendix 2 representing locations of the backbone atoms of at least the core amino acids defining the CRIg binding site for C3b. The three-dimensional configuration of points may be displayed, without limitation, as a holographic image, a stereodiagram, a model, or a computer-displayed image, wherein the CRIg binding site for C3b forms a crystal having the space group symmetry C2221.

In yet another aspect, the invention concerns a machine-readable data storage medium comprising a data storage material encoded with machine-readable data, wherein a machine programmed with instructions for using such data displays a graphical three-dimensional representation of at least one molecule or molecular complex comprising at least a portion of a CRIg binding site for C3b, the binding site defined by a set of points having a distance less than about 4.7 Å from points representing the atoms of the amino acids as represented by the structure coordinates listed in Appendix 2.

In a further aspect, the invention concerns a method of identifying a CRIg agonist comprising designing a compound that mimics the C3b binding site of CRIg.

The invention further concerns a chemical entity identified by (a) employing computational or experimental means to perform a fitting operation between the chemical entity and the three-dimensional structure of a CRIg polypeptide or a C3b:CRIg complex; and (b) analyzing the data obtained in step (a) to determine the characteristics of the association between the chemical entity and the native CRIg or the C3b:CRIg complex.

In a particular embodiment, the chemical entity above interferes with the in vivo or in vitro association between CRIg and C3b.

The invention further concerns a molecule or a molecular complex comprising at least a portion of the C3b binding region of a native sequence CRIg molecule, or a conservative amino acid substitution variant thereof.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Definitions

Figure 1:
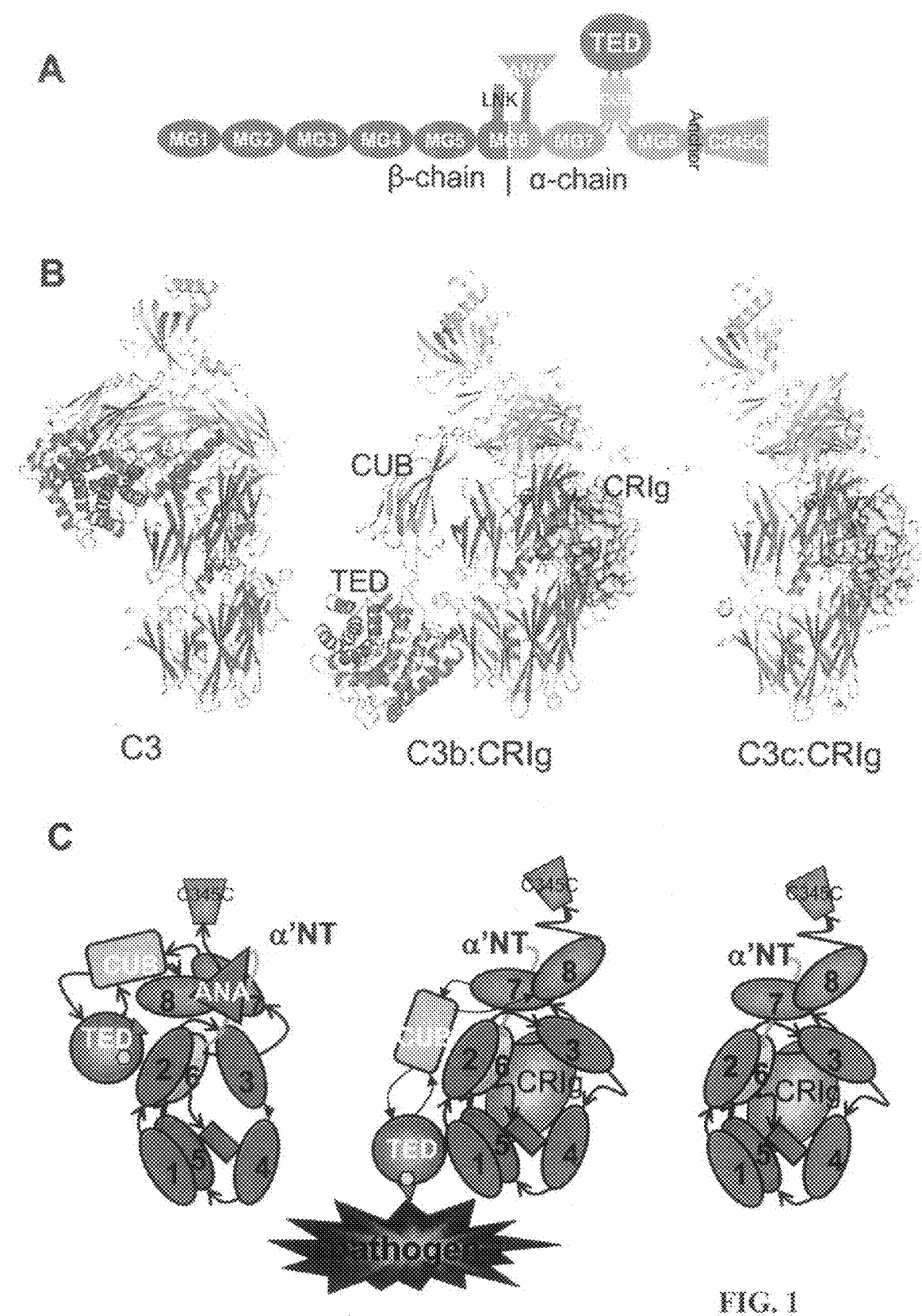
FIG. 1. Domain architecture and over all structure of C3 and the C3b:CRIg and C3c:CRIg complexes. (A) Domain organization of C3, the β-chain is depicted in green, the α-chain in cyan (ANA domain), orange, (CUB), blue (TED), and violet. The red sphere indicates the position of the thioester. (B) Ribbon diagrams of native C3 (left), C3b in complex with CRIg (center), and C3c in complex with CRIg. The color scheme of FIG. 1A is used and the surface of CRIg is shown in yellow. Note the huge movement of the CUB and TED domain when comparing C3 and C3b. After activation the TED translates and rotates in comparison to the remainder of C3b, Cys988 moves more than 80 Å. (C) Schematic depiction of the FIG. 1B; the potential covalent attachment of C3b to a pathogen is indicated in the C3B:CRIg complex.

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

The terms "CRIg," "PRO362," "JAM4," and "STIgMA" are used interchangeably, and refer to native sequence and variant CRIg polypeptides.

A "native sequence" CRIg, is a polypeptide having the same amino acid sequence as a CRIg polypeptide derived from nature, regardless of its mode of preparation. Thus, native sequence CRIg can be isolated from nature or can be produced by recombinant and/or synthetic means. The term "native sequence CRIg", specifically encompasses naturally-occurring truncated or secreted forms of CRIg (e.g., an extracellular domain sequence), naturally-occurring variant forms (e.g., alternatively spliced forms) and naturally-occurring allelic variants of CRIg. Native sequence CRIg polypeptides and fragments thereof specifically include the 321 amino acids long human CRIg polypeptide of SEQ ID NO: 1 with or without the N-terminal signal sequence, with or without the initiating methionine at position 1, and with or without any or all of the transmembrane domain at about amino acid positions 277 to 307 of SEQ ID NO: 1. Native sequence CRIg polypeptides and fragments thereof further include the full-length 399 amino acids long human CRIg polypeptide of SEQ ID NO: 2 (huCRIg, or huCRIg-long), with or without an N-terminal signal sequence, with or without the initiating methionine at position 1, and with or without any or all of the transmembrane domain at about amino acid positions 277 to 307 of SEQ ID NO: 2. In a still further embodiment, the native sequence CRIg polypeptide or a fragment thereof is the 305-amino acid, short form of human CRIg (huCRIg-short, SEQ ID NO: 3), with or without an N-terminal signal sequence, with or without the initiating methionine at position 1, and with or without any or all of the transmembrane domain at about positions 183 to 213 of SEQ ID NO: 3. In a different embodiment, the native sequence CRIg polypeptide or a fragment thereof is a 280 amino acids long, full-length murine CRIg polypeptide of SEQ ID NO: 4 (muCRIg), with or without an N-terminal signal sequence, with or without the initiating methionine at position 1, and with or without any or all of the transmembrane domain at about amino acid positions 181 to 211 of SEQ ID NO: 4. The native sequence CRIg polypeptide or a fragment thereof can also be the rat CRIg polypeptide of SEQ ID NO: 5, with or without the N-terminal signal sequence, with or without the initiating methionine, and with or without any or all of the transmembrane domain. The term further specifically includes the bovine CRIg polypeptide of SEQ ID NO: 6 and the monkey CRIg polypeptide of SEQ ID NO 7, each with or without the N-terminal signal sequence, with or without the initiating methionine, and with or without any or all of the transmembrane domain in the respective sequence.

"CRIg variant" means an active CRIg polypeptide as defined below having at least about 80% amino acid sequence identity to a native sequence CRIg polypeptide. In a particular embodiment, the CRIg variant has at least about 80% amino acid sequence homology with the sequence of a native sequence mature, full-length CRIg polypeptide. Such CRIg polypeptide variants include, for instance, CRIg polypeptides wherein one or more amino acid residues are inserted, substituted and/or deleted, at the N- or C-terminus of the native sequence. Other variants have one or more amino acids inserted, substituted and/or deleted within the transmembrane regions of the native polypeptide sequences.

Ordinarily, a CRIg variant will have at least about 80% amino acid sequence identity, or at least about 85% amino acid sequence identity, or at least about 90% amino acid sequence identity, or at least about 95% amino acid sequence identity, or at least about 98% amino acid sequence identity, or at least about 99% amino acid sequence identity with the mature amino acid sequence from within any of SEQ ID NOS: 1-7. Preferably, the highest degree of sequence identity occurs within the extracellular domains (ECDs) (amino acids 1 or about 21 to X of SEQ ID NO: 1 or 2, where X is any amino acid residue from position 271 to 281; or amino acids 1 or about 21 to X of SEQ ID NO: 3, where X is any amino acid residue from position 178 to 186, or amino acids 1 or about 21 to X of SEQ ID NO: 4, where X is any amino acid residue from position 176 to 184), for example.

The CRIg (PRO362) "extracellular domain" or "ECD" refers to a form of the CRIg polypeptide, which is essentially free of the transmembrane and cytoplasmic domains of the respective full length molecules. Ordinarily, the CRIg ECD will have less than 1% of such transmembrane and/or cytoplasmic domains and preferably, will have less than 0.5% of such domains. As discussed above, optionally, CRIg ECD will comprise amino acid residues 1 or about 21 to X of SEQ ID NO: 1, 2, 3, or 4, where X is any amino acid from about 271 to 281 in SEQ ID NO: 1 or 2, any amino acid from about 178 to 186 in SEQ ID NO: 3, and any amino acid from about 176 to 184 in SEQ ID NO: 4.

"Percent (%) amino acid sequence identity" with respect to the CRIg sequences is defined as the percentage of amino acid residues in a candidate sequence that are identical with the amino acid residues in the CRIg sequence, respectively, after aligning the sequences, introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Unless specifically mentioned otherwise, alignment is performed using the default parameters of the chosen software. Sequence identity is then calculated relative to the longer sequence, i.e. even if a shorter sequence shows 100% sequence identity with a portion of a longer sequence, the overall sequence identity will be less than 100%.

"Percent (%) nucleic acid sequence identity" with respect to the CRIg-encoding sequences is defined as the percentage of nucleotides in a candidate sequence that are identical with the nucleotides in the CRIg-encoding sequence, respectively, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence identity is then calculated relative to the longer sequence, i.e. even if a shorter sequence shows 100% sequence identity with a portion of a longer sequence, the overall sequence identity will be less than 100%.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes nucleic acid molecules contained in cells that ordinarily express an encoded polypeptide where, for example, the nucleic acid molecule is in a chromosomal location different from that of natural cells.

An "isolated" CRIg polypeptide-encoding nucleic acid molecule is a nucleic acid molecule that is identified and separated from at least one contaminant nucleic acid molecule with which it is ordinarily associated in the natural source of the CRIg-encoding nucleic acid. An isolated CRIg polypeptide-encoding nucleic acid molecule is other than in the form or setting in which it is found in nature. Isolated CRIg polypeptide-encoding nucleic acid molecules therefore are distinguished from the encoding nucleic acid molecule(s) as they exists in natural cells. However, an isolated CRIg-encoding nucleic acid molecule includes CRIg-encoding nucleic acid molecules contained in cells that ordinarily express CRIg where, for example, the nucleic acid molecule is in a chromosomal location different from that of natural cells.

The term "complement-associated disease" is used herein in the broadest sense and includes all diseases and pathological conditions the pathogenesis of which involves abnormalities of the activation of the complement system, such as, for example, complement deficiencies. The term specifically include diseases and pathological conditions that benefit from the inhibition of C3 convertase. The term additionally includes diseases and pathological conditions that benefit from inhibition, including selective inhibition, of the alternative complement pathway. Complement-associated diseases include, without limitation, inflammatory diseases and autoimmune diseases, such as, for example, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, macular degenerative diseases and other complement-associated eye conditions, such as age-related macular degeneration (AMD), choroidal neovascularization (CNV), uveitis, diabetic and other ischemia-related retinopathies, endophthalmitis, and other intraocular neovascular diseases, such as diabetic macular edema, pathological myopia, von Hippel-Lindau disease, histoplasmosis of the eye, Central Retinal Vein Occlusion (CRVO), corneal neovascularization, retinal neovascularization, as well as allo-transplantation, hyperacute rejection, hemodialysis, chronic occlusive pulmonary distress syndrome (COPD), asthma, and aspiration pneumonia.

The term "complement-associated eye condition" is used in the broadest sense and includes all eye conditions the pathology of which involves complement, including the classical and the alternative pathways, and in particular the alternative pathway of complement. Complement-associated eye conditions include, without limitation, macular degenerative diseases, such as all stages of age-related macular degeneration (AMD), including dry and wet (non-exudative and exudative) forms, choroidal neovascularization (CNV), uveitis, diabetic and other ischemia-related retinopathies, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. A preferred group of complement-associated eye conditions includes age-related macular degeneration (AMD), including non-exudative (wet) and exudative (dry or atrophic) AMD, choroidal neovascularization (CNV), diabetic retinopathy (DR), and endophthalmitis.

The term "inflammatory disease" and "inflammatory disorder" are used interchangeably and mean a disease or disorder in which a component of the immune system of a mammal causes, mediates or otherwise contributes to an inflammatory response contributing to morbidity in the mammal. Also included are diseases in which reduction of the inflammatory response has an ameliorative effect on progression of the disease. Included within this term are immune-mediated inflammatory diseases, including autoimmune diseases.

The term "T-cell mediated" disease means a disease in which T cells directly or indirectly mediate or otherwise contribute to morbidity in a mammal. The T cell mediated disease may be associated with cell mediated effects, lymphokine mediated effects, etc. and even effects associated with B cells if the B cells are stimulated, for example, by the lymphokines secreted by T cells.

Examples of immune-related and inflammatory diseases, some of which are T cell mediated, include, without limitation, inflammatory bowel disease (IBD), systemic lupus erythematosus, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vaculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic polyneuropathy, hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis, inflammatory and fibrotic lung diseases (e.g., cystic fibrosis), gluten-sensitive enteropathy, Whipple's disease, autoimmune or immune-mediated skin diseases including bullous skin diseases, erythema multiforme and contact dermatitis, psoriasis, allergic diseases of the lung such as eosinophilic pneumonia, idiopathic pulmonary fibrosis and hypersensitivity pneumonitis, transplantation associated diseases including graft rejection, graft-versus host disease, Alzheimer's disease, and atherosclerosis.

"Tumor", as used herein, refers to all neoplastic cell growth and proliferation whether malignant or benign, and all pre-cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinoma, kidney cancer, liver cancer, vulval cancer, thyroid cancer, hepatic carcinoma and various types of head and neck cancer.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In treatment of an immune related disease, a therapeutic agent may directly alter the magnitude of response of a component of the immune response, or render the disease more susceptible to treatment by other therapeutic agents, e.g., antibiotics, antifungals, anti-inflammatory agents, chemotherapeutics, etc.

The "pathology" of a disease, such as a complement-associated disease, includes all phenomena that compromise the well-being of the patient. This includes, without limitation, abnormal or uncontrollable cell growth (neutrophilic, eosinophilic, monocytic, lymphocytic cells), antibody production, auto-antibody production, complement production, interference with the normal functioning of neighboring cells, release of cytokines or other secretory products at abnormal levels, suppression or aggravation of any inflammatory or immunological response, infiltration of inflammatory cells (neutrophilic, eosinophilic, monocytic, lymphocytic) into cellular spaces, etc.

The term "mammal" as used herein refers to any animal classified as a mammal, including, without limitation, humans, domestic and farm animals, and zoo, sports or pet animals such horses, pigs, cattle, dogs, cats and ferrets, etc. In a preferred embodiment of the invention, the mammal is a human.

Administration "in combination with" one or more further therapeutic agents includes simultaneous (concurrent) and consecutive administration in any order.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone, parathyroid hormone, thyroxine, insulin, proinsulin, relaxin, prorelaxin, glycoprotein hormones such as follicle stimulating hormone (FSH), thyroid stimulating hormone (TSH), and luteinizing hormone (LH), hepatic growth factor, fibroblast growth factor, prolactin, placental lactogen, tumor necrosis factor-α and -β, mullerian-inhibiting substance, mouse gonadotropin-associated peptide, inhibin, activin, vascular endothelial growth factor, integrin, thrombopoietin (TPO), nerve growth factors such as NGF-β platelet-growth factor, transforming growth factors (TGFs) such as TGF-α and TGF-β, insulin-like growth factor-I and -II, erythropoietin (EPO), osteoinductive factors, interferons such as interferon-α, -β, and -γ, colony stimulating factors (CSFs) such as macrophage-CSF (M-CSF), granulocyte-macrophage-CSF (GM-CSF), and granulocyte-CSF (G-CSF), interleukins (ILs) such as IL-1, IL-1α, IL-2, IL-3, IL-4, IL-5, IL-6, IL-7, IL-8, IL-9, IL-11, IL-12, a tumor necrosis factor such as TNF-α or TNF-β, and other polypeptide factors including LIF and kit ligand (KL). As used herein, the term cytokine includes proteins from natural sources or from recombinant cell culture and biologically active equivalents of the native sequence cytokines.

"Therapeutically effective amount" is the amount of active CRIg, CRIg agonists and antagonists which is required to achieve a measurable improvement in the state, e.g. pathology, of the target disease or condition, such as, for example, a complement-associated disease or condition, or cancer.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42 C; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a polypeptide of the invention fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" in the context of variants of the CRIg polypeptides of the invention refers to form(s) of such polypeptides which retain the biological and/or immunological activities of a native or naturally-occurring polypeptide of the invention. A preferred biological activity is the ability to bind C3b, and/or to affect complement or complement activation, in particular to inhibit the alternative complement pathway and/or C3 convertase. Inhibition of C3 convertase can, for example, be measured by measuring the inhibition of C3 turnover in normal serum during collagen- or antibody-induced arthritis, or inhibition of C3 deposition is arthritic joints.

"Biological activity" in the context of an antibody, polypeptide or another molecule that mimic CRIg biological activity, and can be identified by the screening assays disclosed herein (e.g. an organic or inorganic small molecule, peptide, etc.) refers, in part, to the ability of such molecules to bind C3b and/or to affect complement or complement activation, in particular, to inhibit the alternative complement pathway and/or C3 convertase.

The term CRIg "agonist" is used in the broadest sense, and includes any molecule that mimics a qualitative biological activity (as hereinabove defined) of a native sequence CRIg polypeptide.

The term "antagonist" is used in the broadest sense, and includes any molecule that partially or fully blocks, inhibits, or neutralizes a qualitative biological activity of a native polypeptide, such as a native sequence CRIg polypeptide.

Suitable agonist or antagonist molecules specifically include agonist or antagonist antibodies or antibody fragments, fragments, fusions or amino acid sequence variants of native polypeptides of the invention, peptides, small molecules, including small organic molecules, etc.

A "small molecule" is defined herein to have a molecular weight below about 600, preferably below about 1000 daltons.

The term "antibody" is used in the broadest sense and specifically covers, without limitation, single anti-CRIg monoclonal antibodies (including agonist, antagonist, and neutralizing antibodies) and anti-CRIg antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas. The term "antibody" is used in the broadest sense and specifically covers, without limitation, intact monoclonal antibodies, polyclonal antibodies, multispecific antibodies (e.g. bispecific antibodies) formed from at least two intact antibodies, and antibody fragments so long as they exhibit the desired biological activity.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et. al., *NIH Publ. No.* 91-3242, Vol. I, pages 647-669 (1991)). The constant domains are not involved directly in binding an antibody to an antigen, but exhibit various effector functions, such as participation of the antibody in antibody-dependent cellular toxicity.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10):1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment. The designation "Fc" reflects the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called γ, μ, δ, α, and ε, respectively. The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 [1975], or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 [1991] and Marks et al., J. Mol. Biol., 222: 581-597 (1991), for example. See also U.S. Pat. Nos. 5,750,373, 5,571,698, 5,403,484 and 5,223,409 which describe the preparation of antibodies using phagemid and phage vectors.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which several or all residues from a complementarity-determining region (CDR) of the recipient are replaced by residues from a CDR of a non-human species (donor antibody) such as mouse, rat or rabbit having the desired specificity, affinity, and capacity. In some instances, certain Fv framework region (FR) residues of the human immunoglobulin can also be replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*, 321: 522-525 (1986); Reichmann et al., *Nature*, 332: 323-329 [1988]; and Presta, *Curr. Op. Struct. Biol.*, 2: 593-596 (1992). The humanized antibody includes a "primatized" antibody where the antigen-binding region of the antibody is derived from an antibody produced by immunizing macaque monkeys with the antigen of interest. Antibodies containing residues from Old World monkeys are also possible within the invention. See, for example, U.S. Pat. Nos. 5,658,570; 5,693,780; 5,681,722; 5,750,105; and 5,756,096.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90: 6444-6448 (1993).

An "isolated" polypeptide, such as an antibody, is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the polypeptide, including antibodies, will be purified (1) to greater than 95% by weight of the antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated compound, e.g. antibody or other polypeptide, includes the compound in situ within recombinant cells since at least one component of the compound's natural environment will not be present. Ordinarily, however, isolated compound will be prepared by at least one purification step.

The word "label" when used herein refers to a detectable compound or composition which is conjugated directly or indirectly to a compound, e.g. antibody or polypeptide, so as to generate a "labeled" compound. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the compound of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Chronic" administration refers to administration of the agent(s) in a continuous mode as opposed to an acute mode, so as to maintain the desired effect for an extended period of time.

"Intermittent" administration is treatment that is not consecutively done without interruption, but rather is cyclic in nature.

Administration "in combination with" one or more further therapeutic agents includes simultaneous (concurrent) and consecutive administration in any order.

A "subject" is a vertebrate, preferably a mammal, more preferably a human.

The term "mammal" is used herein to refer to any animal classified as a mammal, including, without limitation, humans, domestic and farm animals, and zoo, sports, or pet animals, such as sheep, dogs, horses, cats, cows, etc. Preferably, the mammal herein is human.

An "effective amount" is an amount sufficient to effect beneficial or desired therapeutic (including preventative) results. An effective amount can be administered in one or more administrations.

Modes of Carrying Out the Invention

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

Crystal Structure of CRIg and the C3b:CRIg and C3c Complexes

Polypeptides, including the CRIg molecules, have a three-dimensional structure determined by the primary amino acid sequence and the environment surrounding the polypeptide. This three-dimensional structure establishes the activity, stability, binding affinity, binding specificity, and other biochemical attributes of the polypeptide. Thus, knowledge of the three-dimensional structure of a protein provides much guidance in designing agents that mimic, inhibit, or improve its biological activity.

The three-dimensional structure of a polypeptide may be determined in a number of ways. Many of the most precise methods employ x-ray crystallography (Van Holde, *Physical Biochemistry* (Prentice Hall: N.J., 1971), pp. 221-239). This technique relies on the ability of crystalline lattices to diffract x-ray or other forms of radiation. Diffraction experiments suitable for determining the three-dimensional structure of macromolecules typically require high-quality crystals. Unfortunately, such crystals have been unavailable for IGF-1 as well as many other proteins of interest. Crystals have been described for M-CSF (EP 668,914B1), CD40 ligand (WO 97/00895), and a BC2 Fab fragment (WO 99/01476), for example.

Various methods for preparing crystalline proteins and polypeptides are known in the art (McPherson et al., "Preparation and Analysis of Protein Crystals," McPherson (Robert E. Krieger Publishing Company, Malabar, Fla., 1989); Weber, Advances in Protein Chemistry, 41: 1-36 (1991); U.S. Pat. Nos. 4,672,108 and 4,833,233). Although there are multiple approaches to crystallizing polypeptides, no single set of conditions provides a reasonable expectation of success, especially when the crystals must be suitable for x-ray diffraction studies. Significant effort is required to obtain crystals of sufficient size and resolution to provide accurate information regarding the structure. For example, once a protein of sufficient purity is obtained, it must be crystallized to a size and clarity that is useful for x-ray diffraction and subsequent structure resolution. Further, although the amino acid sequence of a target protein may be known, this sequence information does not allow an accurate prediction of the crystal structure of the protein. Nor does the sequence information afford an understanding of the structural, conformational, and chemical interactions between a protein and a binding partner with which it interacts, such as CRIg and C3b. Thus, although crystal structures can provide a wealth of valuable information in the field of drug design and discovery, crystals of certain biologically relevant compounds such as CRIg are not readily available to those skilled in the art. High-quality, diffracting crystals of CRIg assist the determination of its three-dimensional structure, which in turn is important for further understanding its biological role and for designing CRIg variants, agonists and antagonists, including, but not limited to, agonist and antagonist antibodies.

In addition to providing structural information, crystalline polypeptides provide other advantages. For example, the crystallization process itself further purifies the polypeptide and satisfies one of the classical criteria for homogeneity. In fact, crystallization frequently provides unparalleled purification quality, removing impurities that are not removed by other purification methods such as HPLC, dialysis, conventional column chromatography, etc. Moreover, crystalline polypeptides are often stable at ambient temperatures and free of protease contamination and other degradation associated with solution storage. Crystalline polypeptides may also be useful as pharmaceutical preparations. Finally, crystallization techniques in general are largely free of problems such as denaturation associated with other stabilization methods (e.g. lyophilization).

The instant invention presents the crystal structure of CRIg alone and in complex with C3b and C3c, respectively. The structure of the C3b:CRIg complex reveals the full extent of conformational changes that occur upon C3 activation and define the binding sites of the complement receptor CRIg. In addition, the consequences of this interaction for proteolytic activity of the alternative pathway convertases are examined.

Specifically, the present invention provides CRIg crystals having approximately the following dimensions: a=30.3 Å, b=50.8 Å, c=62.0 Å. The crystals have a symmetry, or space group, of $P2_12_12_1$. The structural coordinates of the CRIg crystals are provided in Appendix 1.

The invention further provides the crystal structure of the C3b:CRIg complex, which has approximately the following dimensions: a=97.6 Å, b=255.7 Å, c=180.3 Å, and a space group of $C222_1$. The structural coordinates of the CRIg crystals are provided in Appendix 2, and the ribbon structure thereof is shown in FIG. 1B.

The invention additionally provides the crystal structure of the C3c:CRIg complex, which has approximately the following dimensions: a=382.8 Å, b=65.0 Å, c=147.2 Å, β=102.7, and a space group of C2. The structural coordinates of the C3c:CRIg crystals are shown in Appendix 3, and the ribbon structure thereof is shown in FIG. 1C.

The β-chain of C3b, composed of residue 1 to 645, folds into 5 macroglobulin-like domains (MG1-MG5), and N-terminal half of a $6^{th}$ MG domain, an a linker region (LNK) (FIGS. 1A and 1B). The immunoglobulin topology MG domains are arranged in a 'key-ring' like fashion and circle around a central cavity that is about 10 Å wide and 30 Å long. The α-chain of C3b is composed of residues 729:1641 and lacks the C3a or ANA-domain when compared to C3. The N-terminal residues (729:745) of the C3b α-chain, referred to as the α'NT domain, adopt an extended conformation and connect to the residues that form the $2^{nd}$ half of the $6^{th}$ MG domain. Following this, the α-chain contains two additional MG domains (MG7 and MG8) with the CUB domain and the thio-ester domain (TED) inserted between them. Finally, the C-terminal 170 residues of the α-chain form the so-called 'anchor region' and the C345C domain.

As described in Example 1, the conformation of C3b undergoes a dramatic change upon activation. The TED rotates away from the CUB and NG8 domains leaving the residues linking the TED and the CUB domains in a completely different conformation. As part of this conformational change, the Cys residue a position 988 of C3b travels more than 80 Å from its initial, protected nest in the C3 structure to an exposed location.

The crystallization studies described in Example 1 revealed that the binding site for CRIg lies on the opposite side of C3b from the CUB and TED domains, placing CRIg about 40 Å from the TED domain (see FIGS. 1A and 1B).

Figure 2:
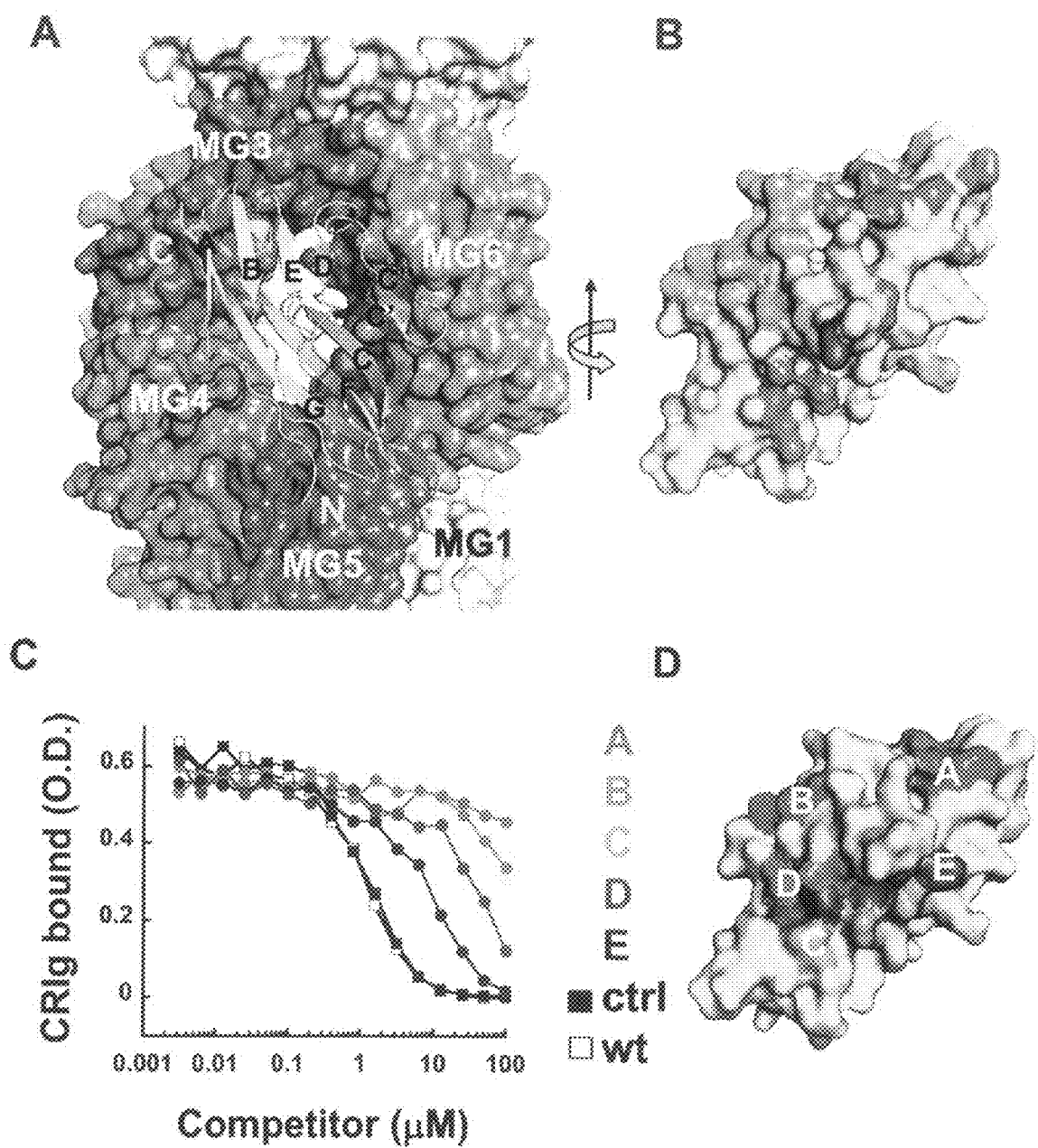
FIG. 2. CRIg binds to the center of the beta chain key-ring of C3b and C3c. (A) Complex between C3c and CRIg. The surface of C3c is shown with residues of the α chain colored white, residues of MG1, MG2, MG3, MG4, MG6, and LNK domain of the β chain are colored white, orange, red, light green, blue, and dark green, respectively. CRIg is depicted as a ribbon diagram, with all β-strands and the N- and C-termini labeled. (B) Surface representation of CRIg, rotated 180 degrees around the Y-axis from FIG. 2A). All atoms that are have a distance of less that 4.5 Å to C3c/C3b are colored like the residues they are contacting in FIG. 2A). (C) Relative affinity of CRIg wildtype and color coded CRIg mutants. The affinity was determined by competition of the various CRIg proteins with CRIg-LFH bound to C3b coated on the plate. CRIg-LFH binding was detected using an anti-FLAG antibody. (D) Surface of CRIg depicting the CRIg mutations used in the binding studies shown in FIG. 2C. Mutated residues are colored according to the binding curve they represent in FIG. 2C.

The binding interface between CRIg and C3c or C3b is large, discontinuous, and buries a total of about 2670 $Å^2$ of solvent accessible surface (FIG. 2A). CRIg contacts C3b with residues from the A',G,G,C,C',C" sheet with the majority of interactions formed by resides and loops in the vicinity of strands C' and C". The hairpin loop connecting C' and C" protrudes into the breach that is formed in the center of the key-ring shaped β-chain of C3b. On the C3b side of the interface, domains MG3, MG4, MG5, MG6, LNK and MG6 all contribute to CRIg binding, with MG3 and MG6 being responsible for about 30% and 40% of the buried interface, respectively (see, FIG. 2B). The MG3 domain is believed to play an important role in gating the binding of CRIg to C3b (and C3c). In addition, a relatively small, yet significant 15° rotation of MG3 in comparison to the rest of the C3 molecule is responsible for the relative reorientation of MG3 in respect to the ring of other MG domains that constitute the CRIg binding site. Therefore, coupled to a movement of a helical section in the LNK region, this rotation allows CRIg binding to C3b and C3c. Absent these modest changes, C3 would not latch onto CRIg.

These structure-function findings have been validated by testing of several amino acid substitution variants of CRIg. It has been confirmed that mutations in the NG6 and MG3 binding domains effectively abrogate binding of CRIg to C3b. By contrast, mutations in CRIg surface residues on the opposite side had no effect on the activity of wild-type CRIg.

Design, Preparation and Screening of CRIg Agonists and Antagonists

This invention includes screening assays to identify CRIg agonists, which find utility, for example, in the treatment of complement associated diseases or disorders, such as immune complex and autoimmune diseases, and various inflammatory conditions, including complement-mediated inflammatory tissue damage. The pathology of complement-associated diseases varies, and might involve complement activation for a long or short period of time, activation of the whole cascade, only one of the cascades (e.g. classical or alternative pathway), only some components of the cascade, etc. In some diseases complement biological activities of complement fragments result in tissue injury and disease. Accordingly, inhibitors of complement have high therapeutic potential. Selective inhibitors of the alternative pathway would be particularly useful, because clearance of pathogens and other organisms from the blood through the classical pathway will remain intact.

Agonists of the CRIg polypeptides will mimic a qualitative biological activity of a native sequence CRIg polypeptide. Preferably, the biological activity is the ability to bind C3b, and/or to affect complement or complement activation, in particular to inhibit the alternative complement pathway and/or C3 convertase. Agonists include, for example, the immunoadhesins, peptide mimetics, and non-peptide small organic molecules mimicking a qualitative biological activity of a native CRIg as well as agonist antibodies, including antibody fragments.

Immunoadhesins are antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

Peptide mimetics include, for example, peptides containing non-naturally occurring amino acids provided the compound retains CRIg biological activity as described herein. Similarly, peptide mimetics and analogs may include non-amino acid chemical structures that mimic the structure of important structural elements of the CRIg polypeptides of the present invention and retain CRIg biological activity. The term "peptide" is used herein to refer to constrained (that is, having some element of structure as, for example, the presence of amino acids which initiate a .beta. turn or .beta. pleated sheet, or for example, cyclized by the presence of disulfide bonded Cys residues) or unconstrained (e.g., linear) amino acid sequences of less than about 50 amino acid residues, and preferably less than about 40 amino acids residues, including multimers, such as dimers thereof or there between. Of the peptides of less than about 40 amino acid residues, preferred are the peptides of between about 10 and about 30 amino acid residues and especially the peptides of about 20 amino acid residues. However, upon reading the instant disclosure, the skilled artisan will recognize that it is not the length of a particular peptide but its ability to bind C3b and inhibit C3 convertase, in particular C3 convertase of the alternative complement pathway, that distinguishes the peptide.

The screening and identification of CRIg agonists is greatly facilitated by the disclosure of the crystal structure of CRIg and the C3b:CRIg complex, and by the identification of the binding interface between CRIg and C3b. This information enables the design of compounds that mimic the C3b binding site of CRIg.

In addition, CRIg agonists can be identified by (a) employing computational or experimental means to perform a fitting operation between the chemical entity and the three-dimensional structure of a CRIg polypeptide or a C3b:CRIg complex; and (b) analyzing the data obtained in step (a) to determine the characteristics of the association between the chemical entity and the native CRIg or the C3b:CRIg complex. Based on this information, agonist candidates can be synthesized and their agonistic properties can be verified in biological assays of CRIg activity.

In a particular embodiment, an agonist will be a chemical entity that comprises at least a portion of the C3b binding region of a native sequence CRIg molecule, or a conservative amino acid substitution variant thereof.

Peptide mimetics can be conveniently prepared using solid phase peptide synthesis (Merrifield, J. Am. Chem. Soc. 85:2149 (1964); Houghten, Proc. Natl. Acad. Sci. USA 82:5132 (1985)). Solid phase synthesis begins at the carboxyl terminus of the putative peptide by coupling a protected amino acid to an inert solid support. The inert solid support can be any macromolecule capable of serving as an anchor for the C-terminus of the initial amino acid. Typically, the macromolecular support is a cross-linked polymeric resin (e.g., a polyamide or polystyrene resin). In one embodiment, the C-terminal amino acid is coupled to a polystyrene resin to form a benzyl ester. A macromolecular support is selected such that the peptide anchor link is stable under the conditions used to deprotect the α-amino group of the blocked amino acids in peptide synthesis. If a base-labile α-protecting group is used, then it is desirable to use an acid-labile link between the peptide and the solid support. For example, an acid-labile ether resin is effective for base-labile Fmoc-amino acid peptide synthesis. Alternatively, a peptide anchor link and α-protecting group that are differentially labile to acidolysis can be used. For example, an aminomethyl resin such as the phenylacetamidomethyl (Pam) resin works well in conjunction with Boc-amino acid peptide synthesis. After the initial amino acid is coupled to an inert solid support, the α-amino protecting group of the initial amino acid is removed with, for example, trifluoroacetic acid (TFA) in methylene chloride and neutralizing in, for example, triethylamine (TEA). Following deprotection of the initial amino acid's α-amino group, the next α-amino and sidechain protected amino acid in the synthesis is added. The remaining α-amino and, if necessary, side chain protected amino acids are then coupled sequentially in the desired order by condensation to obtain an intermediate compound connected to the solid support. Alternatively, some amino acids may be coupled to one another to form a fragment of the desired peptide followed by addition of the peptide fragment to the growing solid phase peptide chain.

The condensation reaction between two amino acids, or an amino acid and a peptide, or a peptide and a peptide can be carried out according to the usual condensation methods such as the azide method, mixed acid anhydride method, DCC (N,N'-dicyclohexylcarbodiimide) or DIC (N,N'-diisopropylcarbodiimide) methods, active ester method, p-nitrophenyl ester method, BOP (benzotriazole-1-yl-oxy-tris [dimethylamino]phosphonium hexafluorophosphate) method, N-hydroxysuccinic acid imido ester method, etc, and Woodward reagent K method.

It is common in the chemical syntheses of peptides to protect any reactive side-chain groups of the amino acids with suitable protecting groups. Ultimately, these protecting groups are removed after the desired polypeptide chain has been sequentially assembled. Also common is the protection of the α-amino group on an amino acid or peptide fragment while the C-terminal carboxyl group of the amino acid or peptide fragment reacts with the free N-terminal amino group of the growing solid phase polypeptide chain, followed by the selective removal of the α-amino group to permit the addition of the next amino acid or peptide fragment to the solid phase polypeptide chain. Accordingly, it is common in polypeptide synthesis that an intermediate compound is produced which contains each of the amino acid residues located in the desired sequence in the peptide chain wherein individual residues still carry side-chain protecting groups. These protecting groups can be removed substantially at the same time to produce the desired polypeptide product following removal from the solid phase.

α- and ε-amino side chains can be protected with benzyloxycarbonyl (abbreviated Z), isonicotinyloxycarbonyl (iNOC), o-chlorobenzyloxycarbonyl [Z(2Cl)], p-nitrobenzyloxycarbonyl [Z(NO$_2$)], p-methoxybenzyloxycarbonyl [Z(OMe))], t-butoxycarbonyl (Boc), t-amyloxycarbonyl (Aoc), isobornyloxycarbonyl, adamantyloxycarbonyl, 2-(4-biphenyl)-2-propyloxycarbonyl (Bpoc), 9-fluorenylmethoxycarbonyl (Fmoc), methylsulfonyethoxycarbonyl (Msc), trifluoroacetyl, phthalyl, formyl, 2-nitrophenylsulphenyl (NPS), diphenylphosphinothioyl (Ppt), and dimethylphosphinothioyl (Mpt) groups, and the like.

Protective groups for the carboxyl functional group are exemplified by benzyl ester (OBzl), cyclohexyl ester (Chx), 4-nitrobenzyl ester (ONb), t-butyl ester (Obut), 4-pyridylmethyl ester (OPic), and the like. It is often desirable that specific amino acids such as arginine, cysteine, and serine possessing a functional group other than amino and carboxyl groups are protected by a suitable protective group. For example, the guanidino group of arginine may be protected with nitro, p-toluenesulfonyl, benzyloxycarbonyl, adamantyloxycarbonyl, p-methoxybenzesulfonyl, 4-methoxy-2,6-dimethylbenzenesulfonyl (Nds), 1,3,5-trimethylphenysulfonyl (Mts), and the like. The thiol group of cysteine can be protected with p-methoxybenzyl, trityl, and the like.

Many of the blocked amino acids described above can be obtained from commercial sources such as Novabiochem (San Diego, Calif.), Bachem Calif. (Torrence, Calif.) or Peninsula Labs (Belmont, Calif.).

After the desired amino acid sequence has been completed, the peptide can be cleaved away from the solid support, recovered and purified. The peptide is removed from the solid support by a reagent capable of disrupting the peptide-solid phase link, and optionally deprotects blocked side chain functional groups on the peptide. In one embodiment, the peptide is cleaved away from the solid phase by acidolysis with liquid hydrofluoric acid (HF), which also removes any remaining side chain protective groups. Preferably, in order to avoid alkylation of residues in the peptide (for example, alkylation of methionine, cysteine, and tyrosine residues), the acidolysis reaction mixture contains thio-cresol and cresol scavengers. Following HF cleavage, the resin is washed with ether, and the free peptide is extracted from the solid phase with sequential washes of acetic acid solutions. The combined washes are lyophilized, and the peptide is purified.

Antagonists of native sequence CRIg polypeptides find utility in the treatment of conditions benefiting from excessive complement activation, and enhanced complement-mediated host defense mechanisms. CRIg antagonists, such as antibodies to CRIg, can be used in immunoadjuvant therapy for the treatment of tumors (cancer). It is now well established that T cells recognize human tumor specific antigens. One group of tumor antigens, encoded by the MAGE, BAGE and GAGE families of genes, are silent in all adult normal tissues, but are expressed in significant amounts in tumors, such as melanomas, lung tumors, head and neck tumors, and bladder carcinomas. DeSmet, C. et al, (1996) *Proc. Natl. Acad. Sci. USA,* 93:7149. It has been shown that costimulation of T cells induces tumor regression and an antitumor response both in vitro and in vivo. Melero, I. et al, *Nature Medicine* (1997) 3:682; Kwon, E. D. et al, *Proc. Natl. Acad. Sci. USA* (1997) 94:8099; Lynch, D. H. et al, *Nature Medicine* (1997) 3:625; Finn, O. J. and Lotze, M. T., *J. Immunol.* (1998) 21:114. The CRIg antagonists designed and identified in accordance with the present invention can be administered as adjuvants, alone or together with a growth regulating agent, cytotoxic agent or chemotherapeutic agent, to stimulate T cell proliferation/activation and an antitumor response to tumor antigens. The growth regulating, cytotoxic, or chemotherapeutic agent may be administered in conventional amounts using known administration regimes. Immunostimulating activity by the CRIg antagonists of the invention allows reduced amounts of the growth regulating, cytotoxic, or chemotherapeutic agents thereby potentially lowering the toxicity to the patient.

Although some macrophages are involved in tumor eradication, many solid tumors are known to contain macrophages that support tumor growth (Bingle et al., *J Pathol* 196:254-265 (2002); Mantovani et al., *Trends Immunol* 23:549-555 (2002)). These macrophages may contain CRIg on their surface Antibodies that block the capacity of CRIg to inhibit complement activation could be used to activate complement on tumor cells and help irradicate the tumor through complement-mediated lysis. This approach is expected to be particularly useful in tumors that contain CRIg positive macrophages.

A preferred group of antagonists includes antibodies specifically binding a native CRIg and inhibiting its biological activity.

Exemplary antibodies (both agonists and antagonists) include polyclonal, monoclonal, humanized, bispecific and heteroconjugate antibodies, and antibody fragments.

Antibodies which recognize and bind to the polypeptides of the invention or which act as antagonists thereto may, alternatively be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the CRIg polypeptide of the invention, an antigenic fragment or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against the polypeptide of the invention or having similar activity as the polypeptide of the invention. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxyapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies are preferably monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and coworkers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991); U.S. Pat. No. 5,750,373]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature_Biotechnology 14, 845-51 (1996); Neuberger, Nature Biotechnology 14, 826 (1996); Lonberg and Huszar, Intern. Rev. Immunol. 13 65-93 (1995).

Bispecific antibodies are monoclonal, preferably human or humanized, antibodies that have binding specificities for at least two different antigens. In the present case, one of the binding specificities may be for the polypeptide of the invention, the other one is for any other antigen, and preferably for a cell-surface protein or receptor or receptor subunit.

Methods for making bispecific antibodies are known in the art. Traditionally, the recombinant production of bispecific antibodies is based on the coexpression of two immunoglobulin heavy-chain/light-chain pairs, where the two heavy chains have different specificities (Milstein and Cuello, Nature, 305:537-539 [1983]). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are cotransfected into a suitable host organism. For further details of generating bispecific antibodies see, for example, Suresh et al., Methods in Enzymology, 121:210 (1986).

Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It may be desirable to modify the antibody of the invention with respect to effector function, so as to enhance the effectiveness of the antibody in treating an immune related disease, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B., J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design, 3:219-230 (1989).

The invention also pertains to immunoconjugates comprising an antibody conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. A variety of radionuclides are available for the production of radioconjugated antibodies. Examples include $^{212}$Bi, $^{131}$I, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tissue pre-targeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

CRIg and its agonists and antagonists can be tested in a variety of in vitro and in vivo assays to determine whether they mimic or inhibit a biological activity of a native CRIg molecule.

As a result of their ability to inhibit complement activation, in particular the alternative complement pathway, the CRIg polypeptides find utility in the prevention and/or treatment of complement-associated diseases and pathological conditions. Such diseases and conditions include, without limitation, complement-associated, inflammatory and autoimmune diseases.

Specific examples of complement-associated diseases include, without limitation, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, macular degenerative diseases and other complement-associated eye conditions, such as age-related macular degeneration (AMD), including non-exudative and exudative-type AMD, diabetic retinopathy (DR), and endophthalmitis, uveitis, allo-transplantation, xeno-transplantation, hyperacute rejection, hemodialysis, chronic occlusive pulmonary distress syndrome (COPD), asthma, hereditary angioedema, paroxysma nocturnal hemoglobulinurea, Alzheimers disease, atherosclerosis, aspiration pneumonia, utricaria, such as chronic idiopathic utricaria, hemolytic uremic syndrome, endometriosis, caridogenic shock, ischemia reperfusio injury, multiple schlerosis (MS).

AMD is age-related degeneration of the macula, which is the leading cause of irreversible visual dysfunction in individuals over the age of 60. Two types of AMD exist, non-exudative (dry) and exudative (wet) AMD. The dry, or non-exudative, form involves atrophic and hypertrophic changes in the retinal pigment epithelium (RPE) underlying the central retina (macula) as well as deposits (drusen) on the RPE. Patients with nonexudative ARMD can progress to the wet, or exudative, form of ARMD, in which abnormal blood vessels called choroidal neovascular membranes (CNVMs) develop under the retina, leak fluid and blood, and ultimately cause a blinding disciform scar in and under the retina. Nonexudative ARMD, which is usually a precursor of exudative ARMD, is more common. The presentation of nonexudative ARMD varies; hard drusen, soft drusen, RPE geographic atrophy, and pigment clumping can be present. Complement components are deposited on the RPE early in AMD and are major constituents of drusen. It has been recently reported that complement factor H(CFH) polymorphism accounts for 50% of the attributable risk of AMD (Klein et al., Science 308:385-9 (2005)).

CRIg is particularly useful in the treatment of high risk AMD, including category 3 and category 4 AMD. Category 3 AMD is characterized by the absence of advanced AMD in both eyes, at least one eye having a visual acuity of 20/32 or better, at least one large druse (e.g. 125 µm), extensive (as measured by drusen area) intermediate drusen, or geographic atrophy (GA) that does not involve the center of the macula, or any combination of these. Category 4 high risk AMD is characterized by a visual acuity of 20/32 or better and no advanced AMD (GA involving the center of the macula or features of choroidal neovascularization) in index eye. Fellow eye is characterized by advanced AMD, or visual acuity less than 20/32 attributable to AMD maculopathy. Typically, high risk AMD, if untreated, rapidly progresses into choroidal neovascularization (CNV), at a rate about 10-30-times higher than the rate of progression for category 1 or 2 (not high risk) AMD. Accordingly, CRIg finds utility in the prevention and treatment of CNV and AMD.

A more extensive list of inflammatory conditions as examples of complement-associated diseases includes, for example, inflammatory bowel disease (IBD), systemic lupus erythematosus, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vaculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic polyneuropathy, hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis, inflammatory and fibrotic lung diseases (e.g., cystic fibrosis), gluten-sensitive enteropathy, Whipple's disease, autoimmune or immune-mediated skin diseases including bullous skin diseases, erythema multiforme and contact dermatitis, psoriasis, allergic diseases of the lung such as eosinophilic pneumonia, idiopathic pulmonary fibrosis and hypersensitivity pneumonitis, transplantation associated diseases including graft rejection and graft-versus host disease.

In systemic lupus erythematosus, the central mediator of disease is the production of auto-reactive antibodies to self proteins/tissues and the subsequent generation of immune-mediated inflammation. Antibodies either directly or indirectly mediate tissue injury. Though T lymphocytes have not been shown to be directly involved in tissue damage, T lymphocytes are required for the development of auto-reactive antibodies. The genesis of the disease is thus T lymphocyte dependent. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid is infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stages have necrotic centers surrounded by a mixed inflammatory cell infiltrate. Other manifestations which can occur in RA include: pericarditis, pleuritis, coronary arteritis, interstitial pneumonitis with pulmonary fibrosis, keratoconjunctivitis sicca, and rheumatoid nodules.

Juvenile chronic arthritis is a chronic idiopathic inflammatory disease which begins often at less than 16 years of age. Its phenotype has some similarities to RA; some patients which are rheumatoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing spondylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA-B27 as if it were a foreign peptide expressed by MHC class 1 molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of antinuclear antibodies in many patients. ICAM-1 is often upregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjögren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including bilary cirrhosis, peripheral or sensory neuropathy, and palpable purpura.

Systemic vasculitis includes diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal nocturnal hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet $\beta$ cells; this destruction is mediated by auto-antibodies, and auto-reactive T cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including Multiple Sclerosis; idiopathic demyelinating polyneuropathy or Guillain-Barr syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple Sclerosis is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+ T lymphocytes are the predominant cell type at lesions. The mechanism of oligodendrocyte cell death and subsequent demyelination is not known but is likely T lymphocyte driven.

Inflammatory and Fibrotic Lung Disease, including eosinophilic pneumonia, idiopathic pulmonary fibrosis and hypersensitivity pneumonitis may involve a disregulated immune-inflammatory response. Inhibition of that response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils. Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Transplantation associated diseases, including Graft rejection and Graft-Versus-Host-Disease (GVHD) are T lymphocyte-dependent; inhibition of T lymphocyte function is ameliorative.

In view of the above-listed therapeutic uses of CRIg, potential agonists of CRIg can be evaluated in a variety of cell-based assays and animal models of complement-associated, inflammatory and/or autoimmune diseases or disorders.

Thus, for example, efficacy in the prevention and/or treatment of arthritis can be evaluated in a collagen-induced arthritis model (Terato et al. *Brit. J. Rheum.* 35:828-838 (1966)). Potential arthritis prophylactics/therapeutics can also be screened in a model of antibody-mediated arthritis induced by the intravenous injection of a cocktail of four monoclonal antibodies, as described by Terato et al., *J. Immunol.* 148:2103-8 (1992); Terato et al., *Autoimmunity* 22:137-47 (1995). See, also Example 4 herein. Candidates for the prevention and/or treatment of arthritis can also be studied in transgenic animal models, such as, for example, TNF-α: transgenic mice (Taconic). These animals express human tumor necrosis factor (TNF-α), a cytokine which has been implicated in the pathogenesis of human rheumatoid arthritis. The expression of TNF-α in these mice results in severe chronic arthritis of the forepaws and hind paws, and provides a simple mouse model of inflammatory arthritis.

In recent years, animal models of psoriasis have also been developed. Thus, Asebia (ab), flaky skin (fsn), and chronic proliferative dermatitis (cpd) are spontaneous mouse mutations with psoriasis-like skin alterations. Transgenic mice with cutaneous overexpression of cytokines, such as interferon-γ, interleukin-1α, keratinocyte growth factor, transforming growth factor-α, interferon-6, vascular endothelial growth factor, or bone morphogenic protein-6, can also be used to study in vivo psoriasis and to identify therapeutics for the treatment of psoriasis. Psoriasis-like lesions were also described in $\beta_2$-integrin hypomorphic mice backcrossed to the PL/J strain and in $\beta_1$-integrin transgenic mice, Scid/scid mice reconstituted with CD4$^+$/CD45RB$^{hi}$ T lymphocytes as well as in HLA-B27/h$\beta_2$m transgenic rats. Xenotransplantation models using human skin grafted on to immunodeficient mice are also known. Thus, the compounds of the invention can be tested in the scid/scid mouse model described by Schon, M. P. et al, *Nat. Med.* (1997) 3:183, in which the mice demonstrate histopathologic skin lesions resembling psoriasis. Another suitable model is the human skin/scid mouse chimera prepared as described by Nickoloff, B. J. et al, *Am. J. Path.* (1995) 146:580. For further details see, e.g. Schon, M. P., *J Invest Dermatology* 112:405-410 (1999).

Recombinant (transgenic) animal models can be engineered by introducing the coding portion of the genes of interest into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and other monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA* 82, 6148-615 [1985]); gene targeting in embryonic stem cells (Thompson et al., *Cell* 56, 313-321 [1989]); electroporation of embryos (Lo, *Mol. Cell. Biol.* 3, 1803-1814 [1983]); sperm-mediated gene transfer (Lavitrano et al., *Cell* 57, 717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA* 89, 623-636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry.

The animals may be further examined for signs of immune disease pathology, for example by histological examination to determine infiltration of immune cells into specific tissues. Blocking experiments can also be performed in which the transgenic animals are treated with CRIg or a candidate agonist to determine the extent of effects on complement and complement activation, including the classical and alternative pathways, or T cell proliferation. In these experiments, blocking antibodies which bind to the polypeptide of the invention, are administered to the animal and the biological effect of interest is monitored.

Alternatively, "knock out" animals can be constructed which have a defective or altered gene encoding CRIg, as a result of homologous recombination between the endogenous gene encoding the CRIg polypeptide and altered genomic DNA encoding the same polypeptide introduced into an embryonic cell of the animal. For example, cDNA encoding CRIg can be used to clone genomic DNA encoding CRIg in accordance with established techniques. A portion of the genomic DNA encoding CRIg can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the CRIg polypeptide.

Thus, the biological activity of potential CRIg can be further studied in murine CRIg knock-out mice, as described in Example 7 below.

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test CRIg and CRIg agonists for activity and effectiveness in the treatment of asthma are described by Wolyniec, W. W. et al, *Am. J. Respir. Cell Mol. Biol.* (1998) 18:777 and the references cited therein.

Contact hypersensitivity is a simple in vivo assay of cell mediated immune function. In this procedure, epidermal cells are exposed to exogenous haptens which give rise to a delayed type hypersensitivity reaction which is measured and quantitated. Contact sensitivity involves an initial sensitizing phase followed by an elicitation phase. The elicitation phase occurs when the epidermal cells encounter an antigen to which they have had previous contact. Swelling and inflammation occur, making this an excellent model of human allergic contact dermatitis. A suitable procedure is described in detail in *Current Protocols in Immunology*, Eds. J. E. Cologan, A. M. Kruisbeek, D. H. Margulies, E. M. Shevach and W. Strober, John Wiley & Sons, Inc., 1994, unit 4.2. See also Grabbe, S. and Schwarz, T, *Immun. Today* 19(1):37-44 (1998).

Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T cell reactivity against MHC antigens and minor transplant antigens. A suitable procedure is described in detail in Current Protocols in Immunology, supra, unit 4.3.

An animal model for skin allograft rejection is a means of testing the ability of T cells to mediate in vivo tissue destruction which is indicative of and a measure of their role in anti-viral and tumor immunity. The most common and accepted models use murine tail-skin grafts. Repeated experiments have shown that skin allograft rejection is mediated by T cells, helper T cells and killer-effector T cells, and not antibodies. Auchincloss, H. Jr. and Sachs, D. H., *Fundamental Immunology,* 2nd ed., W. E. Paul ed., Raven Press, NY, 1989, 889-992. A suitable procedure is described in detail in *Current Protocols in Immunology*, supra, unit 4.4. Other transplant rejection models which can be used to test CRIg and CRIg agonists are the allogeneic heart transplant models described by Tanabe, M. et al, *Transplantation* (1994) 58:23 and Tinubu, S. A. et al, *J. Immunol.* (1994) 4330-4338.

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in *Current Protocols in Immunology*, above, unit 4.5.

EAE is a T cell mediated autoimmune disease characterized by T cell and mononuclear cell inflammation and subsequent demyelination of axons in the central nervous system. EAE is generally considered to be a relevant animal model for MS in humans. Bolton, C., *Multiple Sclerosis* (1995) 1:143. Both acute and relapsing-remitting models have been developed. CRIg and its agonists and antagonists can be tested for T cell stimulatory or inhibitory activity against immune mediated demyelinating disease using the protocol described in *Current Protocols in Immunology*, above, units 15.1 and 15.2. See also the models for myelin disease in which oligodendrocytes or Schwann cells are grafted into the central nervous system as described in Duncan, I. D. et al, *Molec. Med. Today* (1997) 554-561.

An animal model of age-related macular degeneration (AMD) consists of mice with a null mutation in Ccl-2 or Ccr-2 gnes. These mice develop cardinal features of AMD, including accumulation of lipofuscin in and drusen beneath the retinal pigmented epithelium (RPE), photoreceptor atrophy and choroidal neovascularization (CNV). These features develop beyond 6 months of age. CRIg and CRIg agonists can be tested for the formation of drusen, photoreceptor atrophy and choroidal neovascularization.

Models of myocardial ischemia-reperfusion can be performed in mice or rats. Animals are tracheostomized and ventilated with a small animal ventilator. Polyethylene catheters are placed in the internal carotid artery and the external jugular vein for measurement of mean arterial blood pressure. Myocardial ischemia reperfusion is initiated by ligating the left anterior descending artery (LAD) with a 6-0 suture. Ischemia is produced by tightening the reversible ligature around the LAD to completely occlude the vessel. The ligature is removed after 30 min and the heart perfused for 4 hours. CRIg and CRIg agonists can be tested for their efficacy by measuring heart infarct size, heart creatine kinase activity, myeloperoxidase activity and immunohistochemistry using anti C3 antibodies A model of diabetic retinopathy involves treatment of mice or rats with streptozotocin. CRIg and CRIg agonists can be tested on their effect on venule dilatation, intraretinal microvascular abnormalities, and neovascularization of the retina and vitreous cavity.

A model for membranopgoliferative glomerulonephritis can be established as follows: Female mice are immunized i.p. with 0.5 mg control rabbit IgG in CFA (day −7). Seven days later (day 0), 1 mg of the rabbit anti-mouse glomerular basement membrane (GBM) antibody is injected i.v. via the tail vein. Elevation of anti-rabbit IgG antibody in the serum is measured by ELISA. 24-h urine samples are collected from the mice in metabolic cages, and mouse renal function is assessed by the measurement of urinary protein in addition to blood urea nitrogen.

Pharmaceutical Compositions

The CRIg agonists and antagonists identified in accordance with the present invention can be administered for the treatment of inflammatory diseases, in the form of pharmaceutical compositions.

Therapeutic formulations are prepared for storage by mixing the active molecule having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Lipofections or liposomes can also be used to deliver the polypeptide, antibody, or an antibody fragment, into cells. Where antibody fragments are used, the smallest fragment which specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g. Marasco et al., *Proc. Natl. Acad. Sci. USA* 90, 7889-7893 [1993]).

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active molecules may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37 C, resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The following examples are offered for illustrative purposes only, and are not intended to limit the scope of the present invention in any way.

All patent and literature references cited in the present specification are hereby expressly incorporated by reference in their entirety.

EXAMPLE 1

Determination of the Crystal Structure of CRIg and the C3b:CRIg Complex

Materials and Methods a. Production and Purification of Mature Human CRIg Protein A DNA fragment encoding residues 1 to 119 of mature human CRIg of SEQ ID NO: 2 (SEQ ID NO: 8) was cloned into the NdeI/BamHI sites of the pET28b expression vector (Novagen), creating a fusion with an N-terminal His-tag followed by a thrombin cleavage site. After purification using Ni-affinity chromatography the fusion protein was digested with thrombin and further purified using size exclusion chromatography. The final protein stock solution had a protein concentration of 20 mg/ml in 10 mM Hepes, 50 mM NaCl, pH 7.2. Selenomethionine labeled protein was obtained using standard protocols.

Purified CRIg was mixed at 5-fold molar access with of C3c or C3b and incubated on ice for 30 minutes. The samples were purified using size exclusion chromatography and concentrated to 10-20 mg/ml in 25 mM Hepes, pH7.2, 50 mM NaCl.

b. Crystallization

All crystals were grown at 19° C. using hanging drop vapor-diffusion method.

CRIg was crystallized by mixing equal the protein solution with equal volumes of reservoir containing 30% PEG 4000, 0.1 M Sodium Acetate, and 0.2 M Ammonium Acetate. Crystals formed after 3 days. Crystals of the C3c:CRIg complex were obtained by mixing the protein solution (20 mg/ml) at a 1:1 ratio with reservoir solution containing 12% PEG 20000, 0.1 M MES, pH6.5. Crystals appeared after 2 weeks. Crystals of the C3b:CRIg complex were obtained by mixing the protein solution (10 mg/ml) with equal volume of reservoir solution containing 12% PEG 20000, 0.1 M MES, pH6.0. Crystals formed after three weeks.

c. Data Collection, Structure Solution and Refinement

For data collection crystals were dipped briefly into a solution containing reservoir with an addition of 20% glycerol and then flash-frozen in liquid nitrogen. All data were collected at ALS beamline 5.0.2. and processed using HKL2000 (Otwinowski, Z. and Minor, W., *Methods Enzymol.* 276:307-326 (1997)). Crystals of uncomplexed CRIg diffracted to 1.2 Å resolution, belong to space group $P2_12_12_1$ with cell parameters of a=30.2, b=50.7 and c=61.9 Å. The structure was solved using multiple anomalous dispersion and program auto-SHARP (G. Bricogne, C. Vonrhein, C. Flensburg, M. Schiltz, W. Paciorek, *Acta Crystallogr D Biol Crystallogr* 59, 2023 (2003)). Refinement using Refmac (G. N. Murshudov, A. A. Vagin, E. J. Dodson, *Acta Crystallogr D Biol Crystallogr* 53, 240 (1997)) and manual adjustments with program O (T. A. Jones, J. Y. Zou, S. W. Cowan, Kjeldgaard, *Acta Crystallogr A* 47 (Pt 2), 110 (1991)) resulted in a model with an Rcryst of 14.9% and Rfree of 17.7%. Crystals of C3c diffracted to 3.1 Å, belong to spacegroup C2 with cell parameters of a=382 Å, b=65.0 Å, c=147.2 Å and β=102.7° and contain two complexes in the asymmetric unit. The structure was solved using AMoRe (Navazza J., *Acta Crystallogr. A* 50:157-163 (1994)) and models of unbound CRIg and C3C (pdb code 2A74). After refinement applying non-crystallographic symmetry restraints the final Rcryst and Rfree were 23.7% and 29.7%, respectively. Crystals of the C3b:CRIg complex diffracted to 4.1 Å resolution, belonged to space group $C222_1$ with cell parameters of a=97.6 Å, b=255.7 Å and c=180.3 Å. After molecular replacement using the C3c:CRIg complex, models of the CUB domain (pdb code 2A73) and the TED domain (1C3D) were manually docked in the electron density map. After rigid body refinement, clear density for the regions linking the TED and CUB domains as well as two glycosylation sites had interpretable density and could be fitted into the electron density. The final model includes a complex of CRIg and C3b without the C345C domain; the latter domain has very weak density and was included in the model with occupancies set to 0.0 to for FIG. 1. The final Rcryst and Rfree were 25.2% and 33.3% respectively.

Results a. Structure Determination

It has been recently determined that the complement receptor CRIg forms complexes with C3b and iC3b, yet is unable to bind the parent molecule C3 (K. Y. Helmy et al., Cell 124, 915 (2006)). To better understand the structural basis for the selectivity of CRIg, the crystal structure of CRIg in its unbound state was determined at high resolution as well as in complex with C3b and C3c (4.1 Å and 3.2 Å resolution, respectively). The structure of unbound CRIg was solved using three-wavelength anomalous dispersion (MAD) phasing (Hendrickson, W. A. et al., *Proteins* 4:77-88 (1988)). The structure of the complexes were subsequently solved by molecular replacement using the coordinates of CRIg and various domains and fragments from structures of C3 (2A73), C3c (2A74), as well as C3d (1C3D) as search models. The C3c:CRIg structure contains 2 molecules in the asymmetric unit, and after refinement using non-crystallographic symmetry restraints, the final R and Rfree were 23.6% and 29.5% respectively. The limited resolution of the C3b:CRIg complex does not allow for extensive positional refinement. However, after modeling of the various linkers and rigid body refinement of individual domains the R and Rfree of the final model are 24.8% and 33.1% respectively, indicating that the structure is of good quality considering the limited resolution.

b. Overall Structure of C3b

The structure of the individual domains of C3b are similar to the recently reported C3 structure (Janssen et al., supra; D. Hourcade, V. M. Holers, J. P. Atkinson, *Adv Immunol* 45, 381 (1989)), however the arrangement of these domains is quite different when compared to C3. In brief, the β-chain of C3b, composed of residues 1 to 645, folds into 5 macroglobulin-like domains (MG1-MG5), the N-terminal half of a $6^{th}$ MG domain, and a linker region (LNK) (FIGS. 1A, B). The immunoglobulin topology MG domains are arranged in a 'key-ring' like fashion and circle around a central cavity that is about 10 Å wide and 30 Å long. The α-chain of C3b is composed of residues 729:1641 and lacks the C3a or ANA-domain when compared to C3. The N-terminal residues (729:745) of the C3b α-chain, referred to as the α'NT domain, adopt an extended conformation and connect to the residues that form the $2^{nd}$ half of the $6^{th}$ MG domain. Following this, the α-chain contains two additional MG domains (MG7 and MG8) with the CUB domain and the thio-ester domain (TED) inserted between them. Finally, the C-terminal 170 residues of the α-chain form the so-called 'anchor region' (3) and the C345C domain.

c. Conformational Changes Upon C3 Activation

Figure 6:
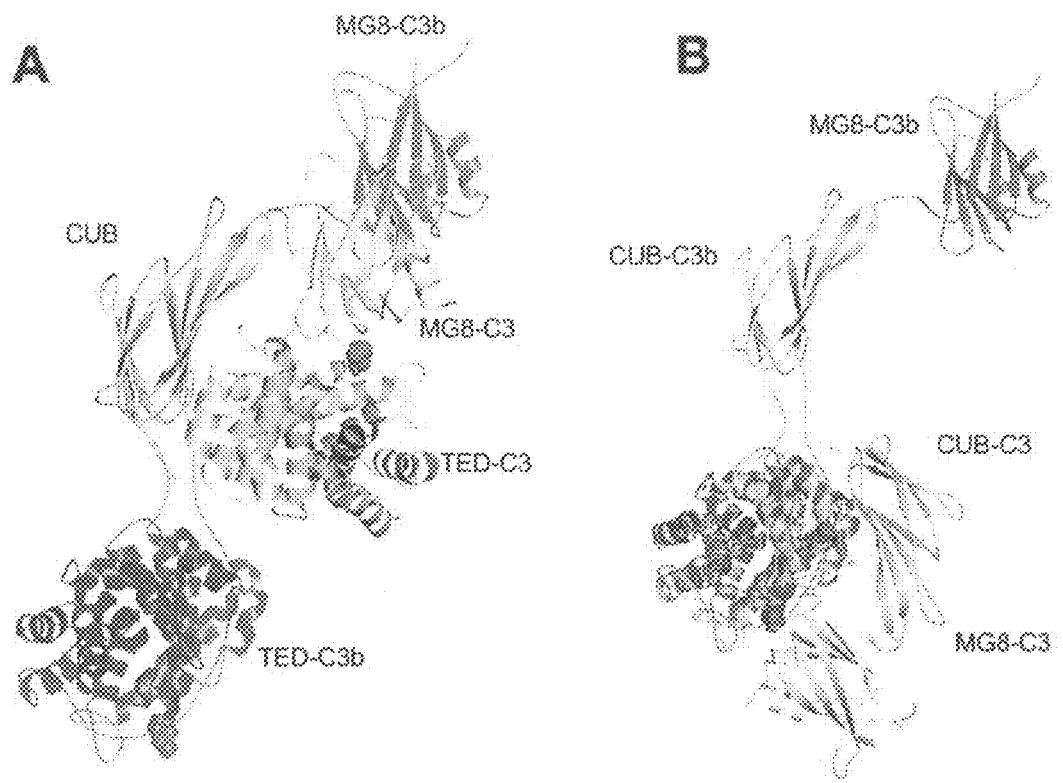
FIG. 6. Differences in domain arrangement between C3 and C3b. Shown are the ribbon diagrams of CUB, TED and MG8-domain (A) Superposition based on the CUB domains of C3 and C3b (both orange). This superposition shows the CUB domain in C3b translates in respect to the MG8 domain of C3 (shown in light violet), while the TED domain undergoes a large rotation upon C3 activation. (C) Superposition based on the TED domain. C3b is shown in darker, C3 in lighter blue. Note the very compact domain arrangement in C3 which is completely open in the C3b structure. The position of Cys988 is indicated with red spheres.

A comparison of the structures of C3, C3b, and C3c, shows that huge conformational changes occur immediately after activation, i.e. the cleavage of C3 to C3b and C3a (FIGS. 1A, B). The release of the ANA-domain which is wedged between the MG3 and the MG8 domain in C3 (F. Fredslund, J et al., supra) allows MG3 and MG8 to rotate. These conformational changes allow further rotations of the MG7 domain and the intriguing movement of the α'NT domain described by Janssen et al., supra, when comparing C3 to C3c. Like in C3c, the α'NT is much more solvent accessible in C3b than in C3 and displays a number of potential binding sites for receptors and regulators of complement activation, CR1, CFH and factor B (J. D. Lambris et al., *J Immunol* 156, 4821 (1996); A. Taniguchi-Sidle, D. E. Isenman, *J Immunol* 153, 5285 (1994); A. E. Oran, D. E. Isenman, *J Biol Chem* 274, 5120 (1999). The largest movements induced by C3 activation however concern the CUB and TED modules. The CUB, packed tightly against MG8 and the TED in C3, moves about 25 Å in respect to MG8 (FIG. 1B and FIG. 6) and only forms loose interactions with MG2 in the C3b structure. In C3 the TED is nestled tightly against the CUB and the MG8 domains which protect from solvent the thio-ester link formed between residues Cys988 and Gln991. Upon activation, the TED rotates away from the CUB and MG8 domains leaving the residues linking the TED and the CUB domains in a completely different conformation; in the course of these changes, Cys988 travels more than 80 Å from its initial, protected nest in the C3 structure to its prominently exposed location in C3b.

Figure 7:
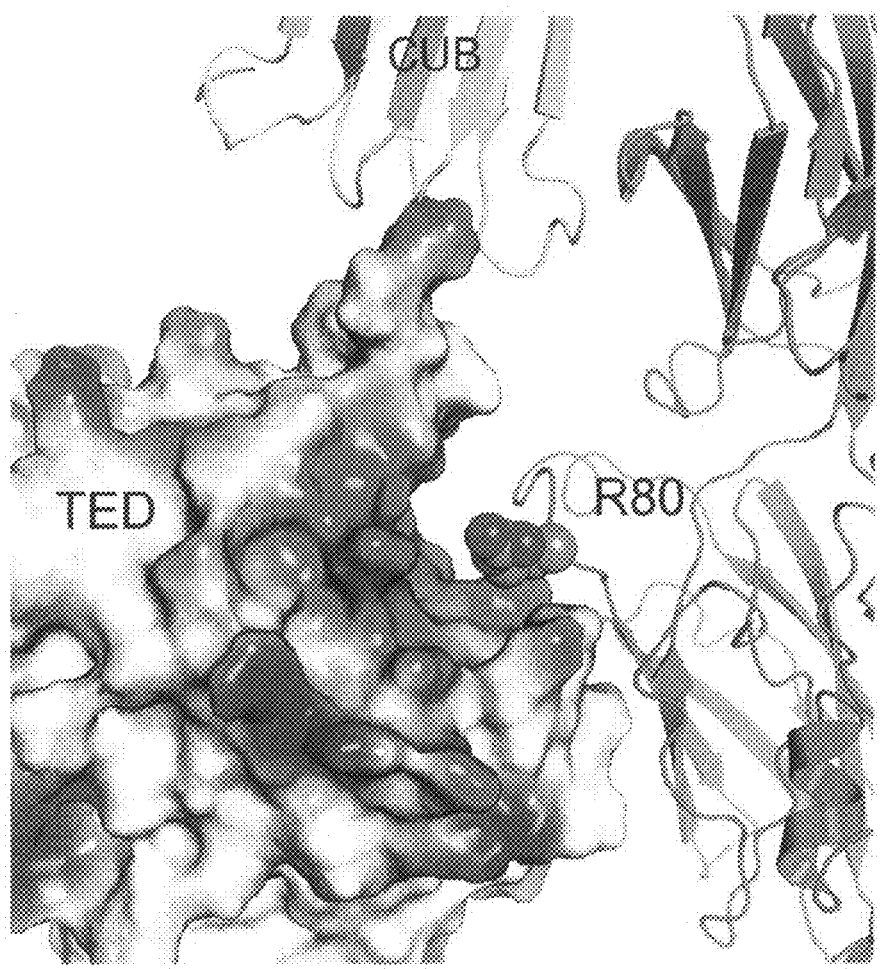
FIG. 7. Interaction between the TED and Arg 80 in C3b. The figure shows a surface representation of the TED colored according to the electrostatic potential as calculated with program pymol (DeLano, M. C. and Cao, Y., *Neuroimaging Clin. N. Am.* 12(1):21-34 (2002)). Red and blue represent negatively and positively charged patches, respectively. The side-chain atoms of R80 are represented in as spheres. Note that Arg80 is close to a highly negatively charged groove on the surface of the TED.

C3 exists in two common allotypes that affect the incidence of inflammatory disease (J. E. Finn et al., *Nephrol Dial Transplant* 9, 1564 (1994)). These variants differ in a single amino acid. The more common allotype, C3F, has a large and positively charged arginine in position 80 while C3S has the small and uncharged glycine. Residue R80 and the surrounding loop does not form any interactions in the structure of C3 or C3c (Janssen et al., supra), and so far no other proteins have been identified that interact with R80. In C3b this loop is responsible for a number of contacts between MG1 and the TED domain and R80 is positioned close to a negatively charged groove on the surface of the TED (FIG. 7). Further experiments are needed to confirm whether the interaction between R80 and the TED domain is responsible for the observed differences between C3S and C3F allotypes.

The α-helical toroid TED modules in C3d and C3 show a number of significant differences (Janssen et al., supra). Most important, residues His1104 and Glu1106—required for the covalent attachment of the TED domain to particle surfaces—are far from each other and from Cys988. In C3d however, these residues are in close proximity, an important prerequisite for the covalent binding reaction. While the resolution of the C3b:CRIg complex presented here does not allow discussion of the precise position of individual amino acid side-chains, it is clear from our structure that the conformation of the TED in C3b is very similar to the C3d structure. The striking conformational shift between C3 and C3b ensures that the TED residues that are important for the binding reactions are solvent exposed and located like a spearhead at the distal tip of the C3b molecule.

d. CRIg Binds to the β-chain of C3b and C3c

Figure 8:
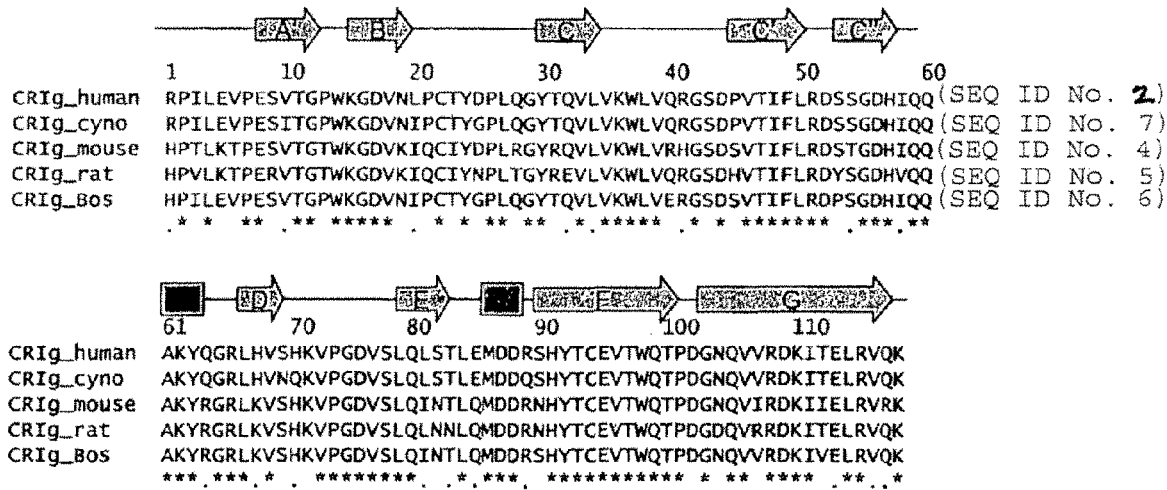
FIG. 8. Sequence alignment of CRIg from different species. Residues in contact with C3b are color coded according to FIG. 2A. Residues numbers refer to human CRIg after the signal sequence. Secondary structural elements are depicted as arrows (strands) and boxes (helices) above the sequence alignment.

The N-terminal domain of CRIg, as predicted by sequence analysis (K. Langnaese, et al., *Biochim Biophys Acta* 1492, 522 (2000)), topologically belongs to the IgV family of immunoglobulin-like domains but shares only about 20% sequence identity with other Ig domains currently deposited in the Protein Data Bank. Like all members of this fold family, the CRIg domain is formed by two β-sheets. One of these sheets is composed by strands A', G, F, C, C' and C", while the other is formed by strands B, E, and D (FIG. 2A and FIG. 8). The domain is further stabilized by a canonical Ig-like disulfide bond formed between two cysteine residues that internally connect strands B and F.

Figure 9:
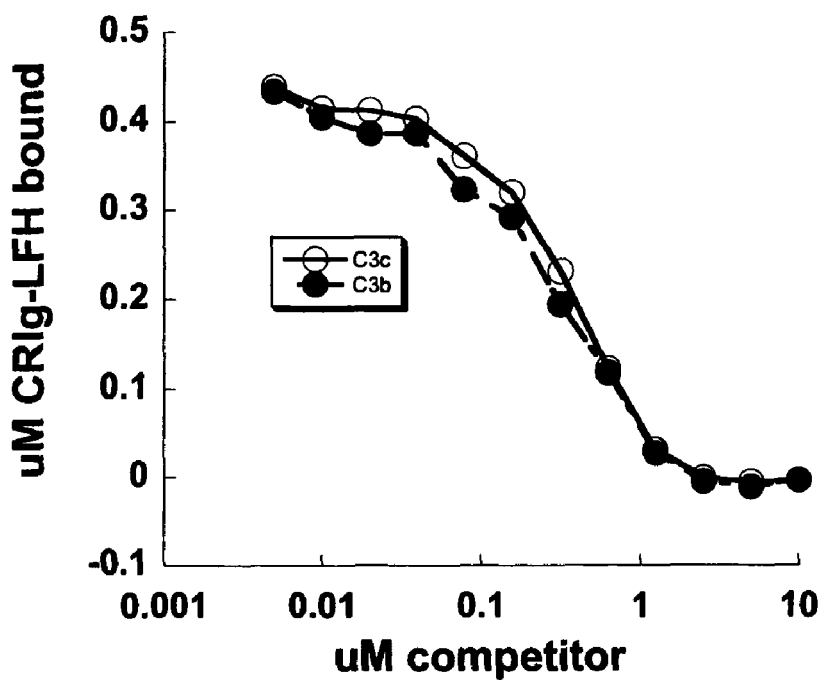
FIG. 9. CRIg has a similar affinity to C3b and C3c. Affinity was determined by competition of increasing concentrations of C3b or C3c with a fixed concentration of CRIg-LFH. CRIg-LFH binding was detected using an anti-FLAG antibody conjugated to HRPO and the absorbence of the TNB reaction product measured spectrophotometrically at 415 nm wavelength.
Figure 10:
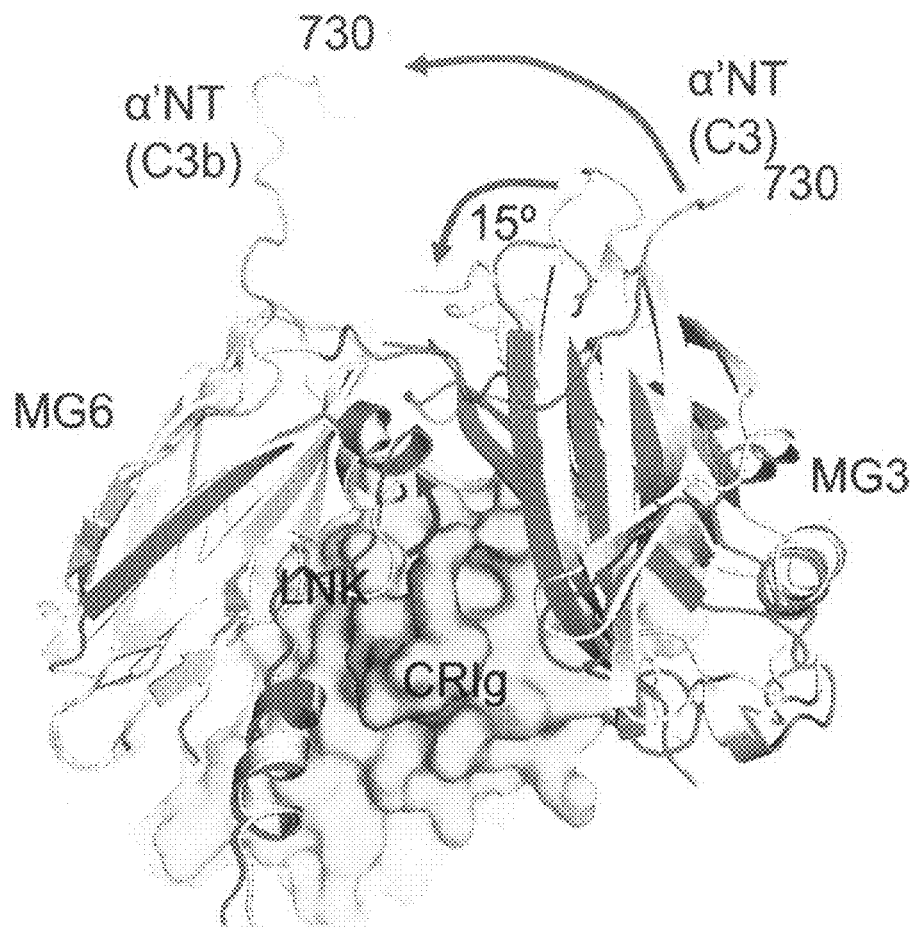
FIG. 10. Local differences between C3 and C3b in the vicinity of the CRIg binding site. The superposition of the C3 and C3b shown here is based on the Cα atoms of the MG6 domain. Parts of C3 are shown in white, with the α'NT domain in blue. The C3b:CRIg complex is depicted in green (β-chain of C3b), violet (α-chain of C3b) with the α'NT domain in blue. CRIg is shown in yellow. Large conformational changes occurring upon C3 activation are indicated with red arrows. Note the large movement of the α'NT domain. The rotation of MG3 in respect to MG6, and the movement of the helical segment (577:590) are required for CRIg binding to C3b and C3c.
Figure 11:
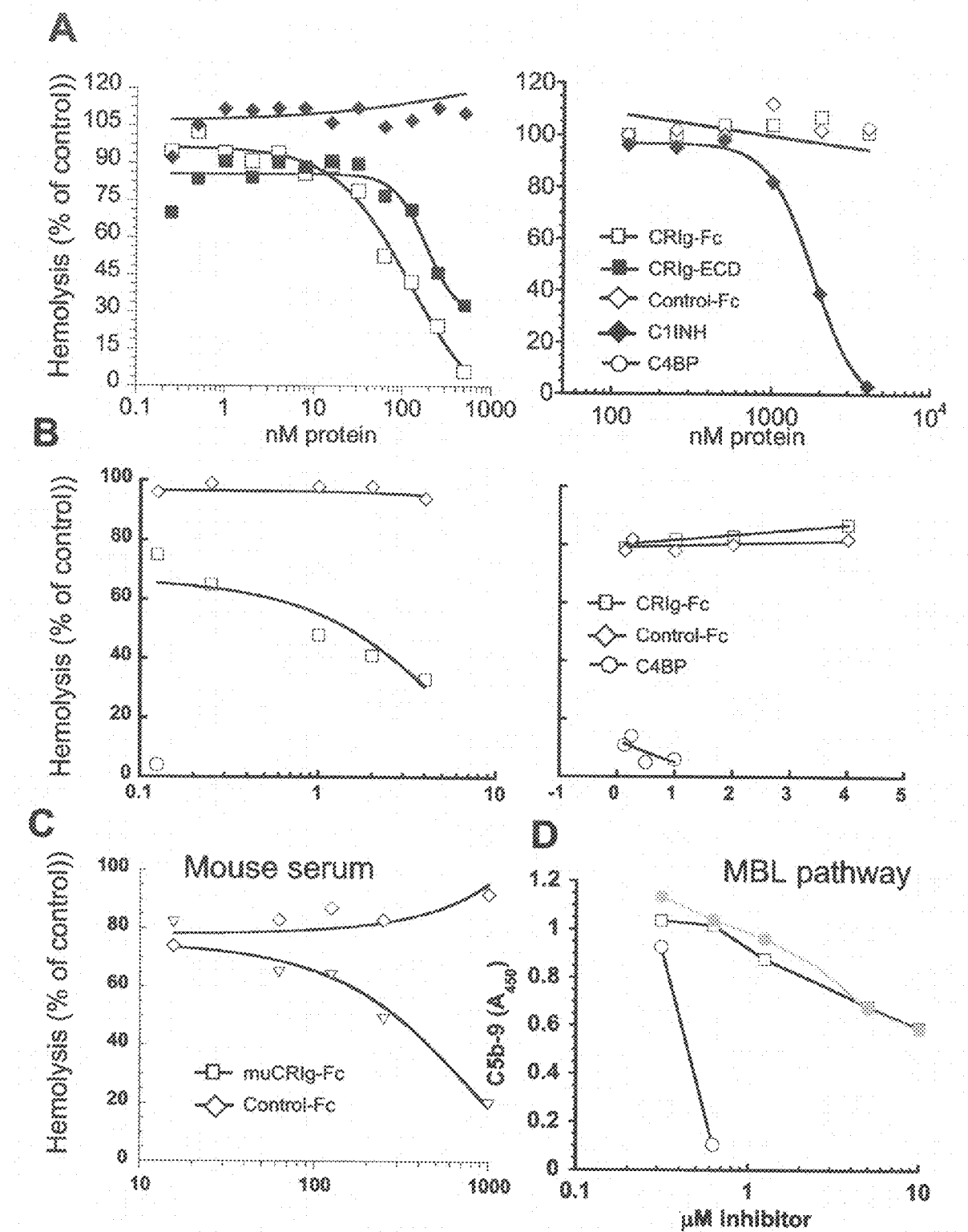
FIG. 11. CRIg selectively inhibits the alternative pathway in human and mouse serum. (A) CRIg inhibits hemolysis of rabbit erythrocytes in C1q deficient serum (alternative pathway, left panel) but not IgM-opsonized sheep erythrocytes in fB deficient serum (classical pathway, right panel). E-IgM and Er were incubated in 5% serum containing different concentrations of CRIg-Fc or CRIg-ECD fusion protein. Hemolysis was stopped by adding ice-cold EDTA and the amount of hemolysis was measured by determining the O.D in the supernatant in a spectrophotometer at 415 nm. IC50 values: CRIg-Fc 127±49 nM (n=6), CRIg-ECD 640±123 nM. (B) CRIg inhibits the alternative pathway of complement initiated by the classical pathway. Complement components of the classical pathway were assembled on SRBCs to generate EAC34 (AP, left panel) or EAC1234 (CP, right panel). Hemolysis was determined as described in (A). (C) murine CRIg-Fc inhibits alternative pathway hemolysis in mouse serum. Er were incubated with 30% mouse serum containing increasing concentrations of murine CRIg-Fc. Hemolysis was measured as described under (A). (D) CRIg does not inhibit the mannose-binding lecting pathway. C5b-9 deposition induced by MBL-pathway activation was measured spectrophotometrically at 415 nm wavelength.
Figure 12:
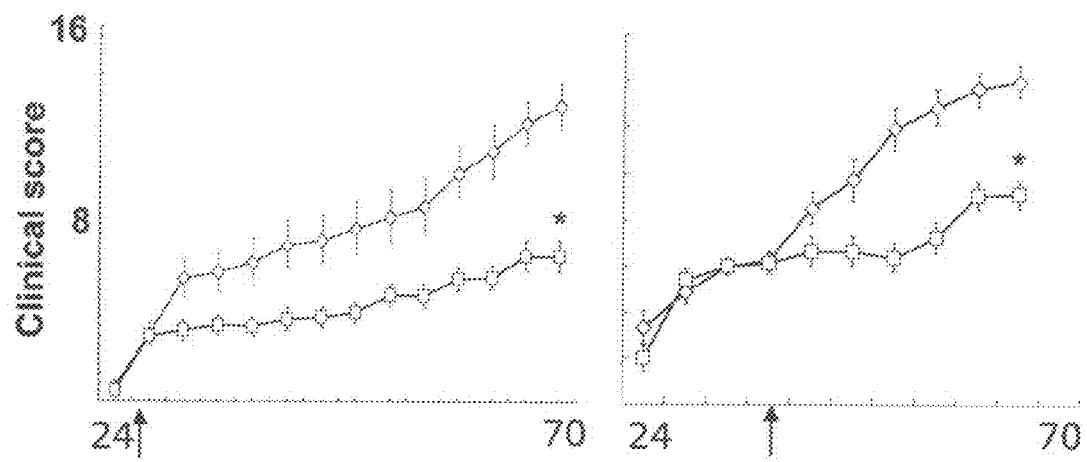
FIG. 12. CRIg inhibits collagen-induced arthritis. (A) Arthritis was induced by immunizing mice twice, on day 0 and day 23, with bovine collagen. Mice were treated with muCRIg-Fc 3 times per week starting on day 24 (prophylactic) or on day 45 when disease was already established (arrows). Clinical scores are a reflection of the ankle thickness. On day 70 following induction of arthritis, mice were euthanized and the joint cortical bone volume (JCBV) was measured (B) and H&E-stained sections evaluated for signs of inflammation (C). (D) Reduction in IL-6 (left panel) and IL-1b (right panel) in joints of mice treated with CRIg-Fc. At the indicated time points following induction of arthritis, mice we euthanized, joints were dissected and processed for cytokine measurements. The increase in cytokine levels due to LPS treatment (first time point) is not affected by muCRIg-Fc treatment. Statistics: * $p<0.01$, ** $p<0.001$, Student's t-test.
Figure 12:
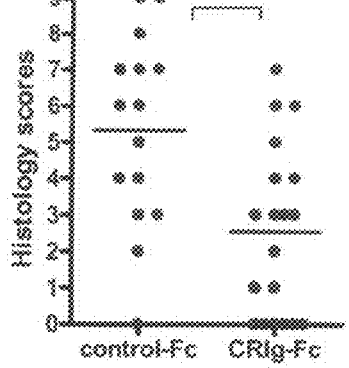
Figure 12:
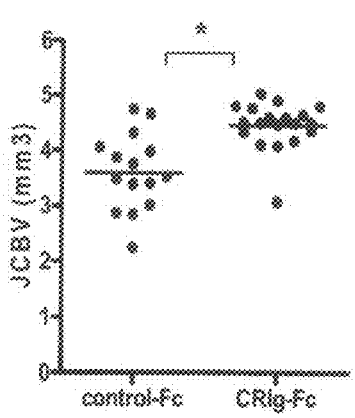
Figure 12:
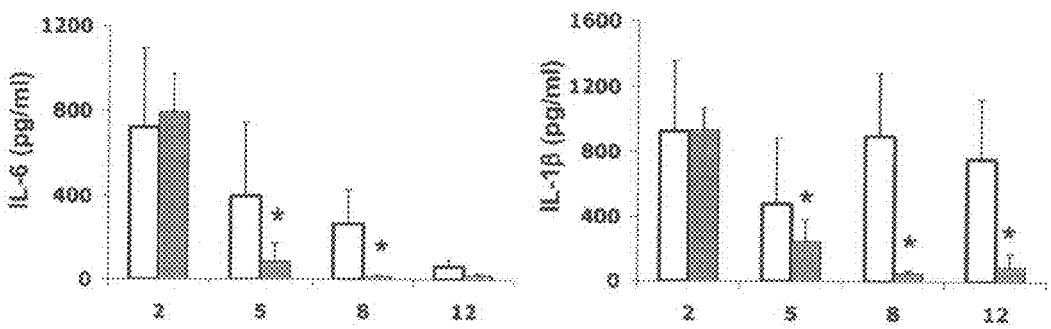
Figure 13:
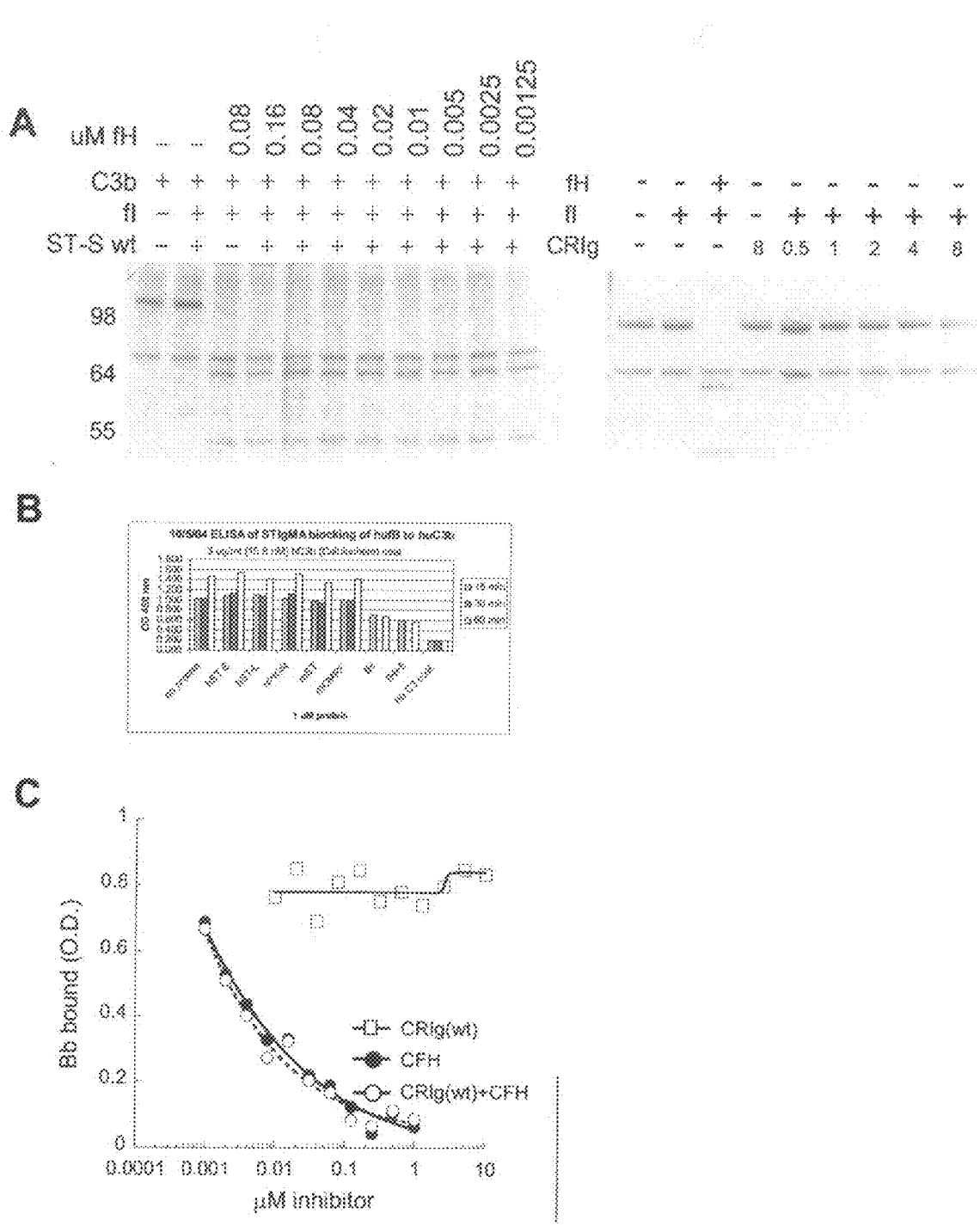
FIG. 13. (A) CRIg does not affect co-factor activity of factor H nor does it have intrinsic co-factor activity. Left panel: A fixed concentration of C3b was mixed with increasing concentrations of factor H in the presence of 4 µM CRIg (wt) or CRIg(C). Co-factor activity was monitored by visualizing the reaction product on a commassie-stained SDS gel to distinguish C3b from iC3b. Right panel: A fixed concentration of C3b and fI was mixed with fH or an increasing concentration of CRIg. (B) CRIg does not inhibit factor B binding to C3b. A fixed concentration of factor B was mixed with increasing concentrations of CRIg. The amount of bound factor B was determined using a polyclonal antibody to fB and a secondary HRPO conjugated ab. (C)CRIg does not decay a C3 convertase. A C3 convertase was formed on a maxisorp plate by incubating C3b, factor B and factor D. The plate was then incubated with increasing concentration of CRIg or factor H. The remaining factor B bound was detected with an anti factor B antibody and a HRPO-conjugated secondary antibody. The result shown is representative of 3 independent experiments.

CRIg engages C3b and C3c in an identical fashion and the arrangement of all contacting domains that are present in both CRIg complexes presented here are very similar. In line with this, the affinity of CRIg for C3b and C3c are comparable (FIG. 9). Superposition of the C3b:CRIg and the C3c:CRIg structures results in RMSD's of less than 0.6 Å for the 642 common Cα positions in the β-chain, and 0.5 Å for the 479 Cα atoms in the α-chain of C3c and C3b.

Unlike all other complement receptors identified to date (J. D. Lambris et al., *J Immunol* 156, 4821 (1996); A. Taniguchi-Sidle, D. E. Isenman, *J Immunol* 153, 5285 (1994); A. E. Oran, D. E. Isenman, *J Biol Chem* 274, 5120 (1999)), CRIg binds primarily to the β-chain of C3b. Comparison of C3c and CRIg structures in their unbound states and in complex with each other reveal that no significant conformational adaptations are required in either of the 2 molecules to enhance binding. The 963 common Cα positions in the C3c structures both unbound (Janssen et al, supra) and bound to CRIg superimpose with an RMSD of 0.8 Å with the largest movements occurring in flexible regions, and only one small loop movement in the MG6 domain (results not shown). The binding site for CRIg lies on the opposite side of C3b from the CUB and TED domains placing CRIg approximately 40 Å away from the TED domain (FIGS. 1A, B).

The binding interface between CRIg and C3c or C3b is large, discontinuous, and buries a total of about 2670 Å of solvent accessible surface (FIG. 2A). CRIg contacts C3b with residues from the A',G,G,C,C',C" sheet with the majority of interactions formed by resides and loops in the vicinity of strands C' and C". The hairpin loop connecting C' and C" protrudes into the breach that is formed in the center of the key-ring shaped β-chain of C3b. On the C3b side of the interface, domains MG3, MG4, MG5, MG6, LNK and MG6 all contribute to CRIg binding, with MG3 and MG6 being responsible for about 30% and 40% of the buried interface, respectively (FIG. 2B). Comparison of C3 and C3b structures suggests a critical role for the MG3 domain in gating the binding of CRIg to C3b and C3c. Aside from the wholesale domain movements that occur upon C3 activation, there are several smaller domain shifts that may have functional importance. Key among these is a relatively subtle, yet significant 15° rotation of MG3 in comparison to the rest of the C3 molecule. This rotation, responsible for the relative reorientation of MG3 in respect to the ring of other MG domains that constitute the CRIg binding site, coupled to a movement of a helical section in the LNK region (FIG. 9) allows CRIg binding to C3b and C3c; absent these modest changes, C3 will not latch onto CRIg.

Important binding parameters are summarized in the following Table 1.

TABLE 1

Data Collection and Refinement Statistics

| | CRIg | C3c:CRIg | C3b:CRIg |
|---|---|---|---|
| Data collection | | | |
| Space group | P2₁2₁2₁ | C2 | C222₁ |
| Cell parameters | a = 30.3, | a = 382.8, | a = 97.6, |
| | b = 50.8, | b = 65.0 | c = 255.7 |
| | c = 62.0 | c = 147.2 | c = 180.3 |
| | | β = 102.7 | |
| Resolution (Å) | 50-1.2 | 50-3.1 | 50-4.1 |
| $R_{sym}{}^b$ | 0.031 (0.22) | 0.097 (0.47) | 0.083 (0.54) |
| Number of observations | 129096 | 183543 | 72321 |
| Unique reflections | 36270 | 62367 | 17385 |
| Completeness (%) | 99 (92.0) | 95.8 (93.7) | 96.1 (86.5) |
| Refinement | | | |
| Content of asymmetric unit | 1 molecule | 2 complexes | 1 complex |
| Resolution (Å) | 20-2.2 | 20-3.1 | 30-4.1 |
| Number of reflections | 200469 | 58910 | 162329 |
| Final $R^c$, $R_{free}$ (F > 0) | 0.149, 0.177 | 0.238, 0.29.8 | 0.252, 0.330 |
| Number of residues | 119 | 2468 | 1521 |
| Number of water molecules | 193 | 0 | 0 |
| Number of Ions | 0 | 2 Ca-Ions | 1 Ca-Ion |
| Number of non-H atoms | 1158 | 19619 | 12072 |
| Rmsd bonds (Å) | 0012 | 0.009 | 0.012 |
| Rmsd angles (°) | 1.59 | 1.25 | 1.36 |

$^a$Numbers in parentheses refer to the highest resolution shell.
$^b R_{sym} = \Sigma |I - <I>|/\Sigma I$. $<I>$ is the average intensity of symmetry related observations of a unique reflection.
$^c R = \Sigma |F_o - F_c|/\Sigma F_o$. $R_{free}$ is calculated as R, but for 5% of the reflections excluded from all refinement.

EXAMPLE 2

CRIg Variants

To functionally validate the importance of the binding interface revealed by the structural complex, the following CRIg mutants were designed and produced, and tested their ability to bind C3b: In the following Table 2, numbers indicate position starting at the signal sequence cleavage site.

TABLE 2

| Mutants | Amino acid substitution |
|---|---|
| A | E85A M86A |
| B | H57A Q59A |
| C | V107S D109R I111E |
| D | L34S K36D L38H |
| E | P91A T93A D95A |
| Cont | H21A T23A D25A |

Mutants were generated using the QuikChange site-directed mutagenesis kit (Stratagene) and primers were designed as per manufacturer's instructions. Results from the binding studies using double or triple mutants agree closely with the crystallographically defined protein-protein contacts (FIG. 2B). Mutations in the MG6 and MG3 binding domains (E85A M86A and H57A Q59A) most effectively abrogated binding of CRIg to C3b (IC50 values were >10,000 and 100 fold higher compared to wt CRIg), illustrating the importance of these domain interactions in CRIg binding. By contrast, mutations in CRIg surface residues located opposite to the binding interface (H21A T23A D25A) showed binding activity similar to the wildtype molecule confirming that these mutations do not alter the overall fold of the molecule. In addition, circular dichroism spectroscopy was further used to assure that all mutant proteins were folded correctly (results not shown).

EXAMPLE 3

CRIg Binding to C3b Inhibits the Alternative Pathway of Complement

Figure 3:
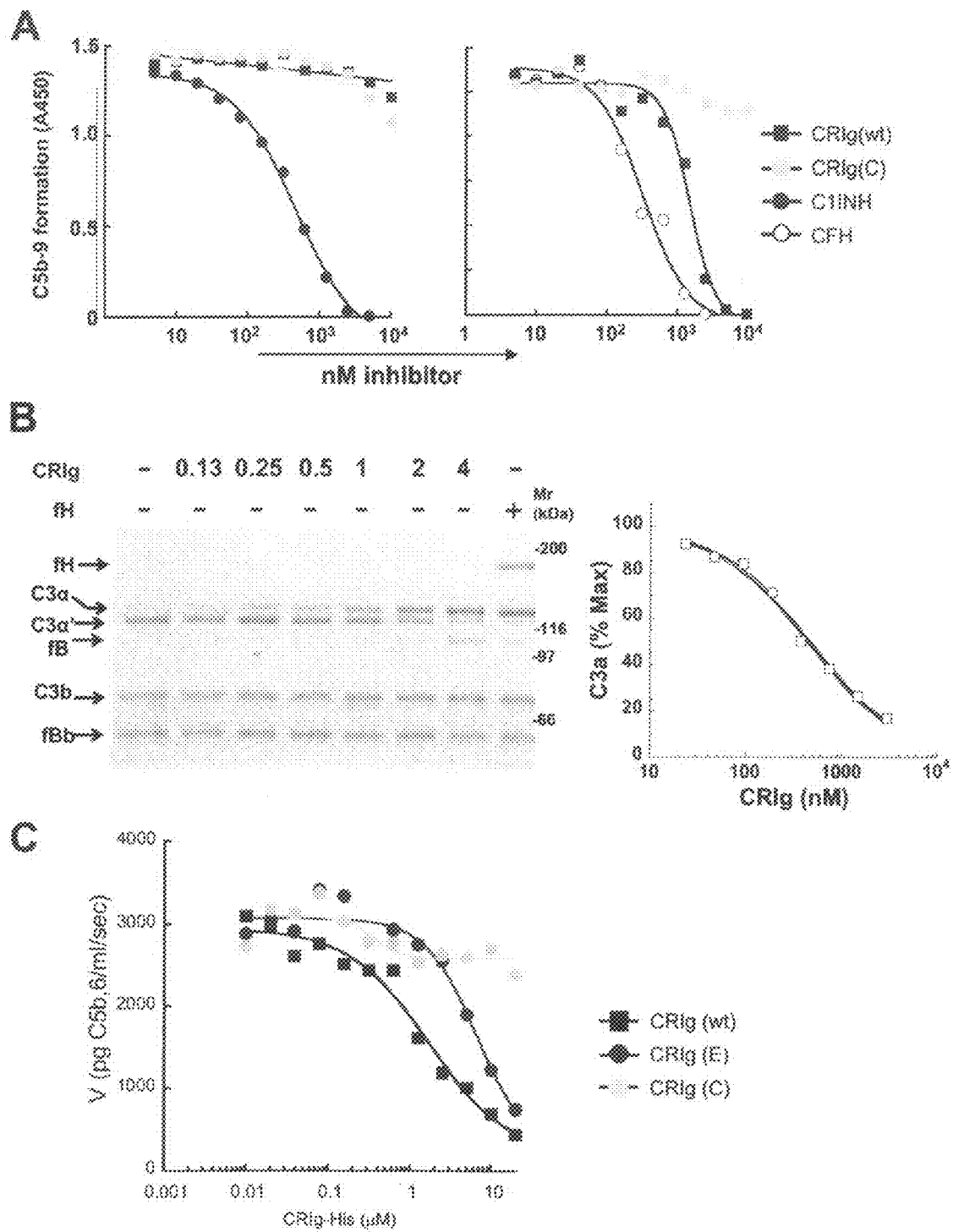
FIG. 3. CRIg inhibits the alternative-(AP), but not classical (CP)-pathway of complement. (A) CRIg inhibits C5b-9 deposition through AP, but not CP or MBL pathway. Complement pathways were reconstituted on a plate coated with LPS (AP) or IgM (CP) and incubated with C1q deficient (AP) or fB deficient (CP) sera. Complement activation was determined by chromogen for detection of bound HRPO-conjugated antibody to C5b-9. The IC50 values for CRIg in the AP assay is 1.49±0.19 µM (n=3). (B) CRIg inhibits fluid-phase C3 convertase activity. C3, fB and fD were incubated in veronal buffer in the presence of increasing concentrations of huCRIg(L)-ECD. The reaction was stopped with EDTA and cleavage products were visualized on a commassie-stained gel (left panel) or by ELISA (right panel). IC50 values for CRIg-ECD is 0.39±0.14 µM (n=3). (C)CRIg inhibits a C5 convertase assembled on the surface of zymosan particles. Zymosan particles were opsonized with C3b in the presence of fB and fD, generating a C5 convertase. A fixed concentration of C5 was mixed with the convertase in the presence of increasing concentrations of CRIg wt or CRIg mutant C(CRIg(C)). Convertase activity was determined by measuring C5b6 produced in fluid phase using a hemolytic assays. The IC50 values: CRIg(Wt) 1.63±0.62 µM (n=3), CRIg (E) 6.52±3.21 µM (n=3).

Since the C5 convertases of both the AP and Classical/MBL pathway contain a C3b subunit (Pangburn and Muller-Eberhard, *Biochem J.*, 235:723 (1986)), we asked whether CRIg could regulate either pathway of complement activation via its binding to C3b. CRIg prevented complement activation through the alternative, but not classical or MBL pathway (FIG. 3a). This inhibitory activity was lost in CRIg mutants that lacked C3b binding activity, confirming that CRIg-C3b binding was directly responsible for disrupting convertase activity. Selective inhibition of the AP by CRIg was further confirmed in cell-based assays which distinguish between the alternative and classical/MBL pathways. The IC50 is decreased 2-fold when CRIg is fused to the Fc portion of IgG (FIG. S6A). Since CRIg is a selective inhibitor of the alternative pathway, CRIg can inhibit alternative pathway hemolysis initiated by the classical pathway (FIG. S6B). Alternative pathway inhibition was retained in mouse CRIg (FIG. S3C) confirming that of CRIg's complement inhibitory activity is phylogenetically conserved.

To further determine the molecular mechanisms by which CRIg inhibits the convertase, the interactions of CRIg with the C3b subunits of the C3 and C5 convertases were studied using purified components. CRIg was able to inhibit the fluid-phase C3 convertase as indicated by a decreased C3a production (FIG. 3B). CRIg also decreased enzymatic activity of a C5 convertase assembled on the surface of zymosan particles (FIG. 3C). The inhibitory activity of various CRIg mutants correlated with their affinity to the C3b subunit, indicating that binding of CRIg to C3b directly regulates activity of the C5 convertase. This shows that CRIg binding to the C3b β-chain prevents cleavage of both C3 and C5 by the convertases of the alternative pathway.

EXAMPLE 4

CRIg Inhibits Complement Activation in Mouse Models of Arthritis

Materials and Methods a. Induction of Arthritis in Mice

Collagen-induced arthritis was performed as described elsewhere (K. H. Barck et al., *Arthritis Rheum* 50, 3377 (2004)). Mice were injected subcutaneously with 4 mg/kg of CRIg-Ig fusion protein starting on day 21, or with 12 mg/kg fusion protein starting at day 36 following the primary immunization. In the CRIg-Ig fusion protein, mouse CRIg extracellular domain was fused to the mouse Fc portion of an IgG1 molecule. Antibody-induced arthritis was induced by the method of Terato and colleagues (K. Terato et al., *J Exp Med* 162, 637 (1985)) using an arthritogenic mAb mixture. Briefly, mice were injected i.v. with 2 mg of anti-CII Ab (2 mg/500 µl/body) from the tail vein, and 3 days later 25 µg of LPS (25 µg/100 µl/body) was injected i.p. Bone volume measurement and histological examination were performed as described elsewhere (Barck et al., supra).

b. Measurement of Cytokine Concentration in Arthritic Hind Paws

Hind footpads of sacrificed mice were cut at the borderline of fur growth and frozen in liquid $N_2$. The footpads were homogenized in ice-cold RIPA lysis buffer supplemented with 1 Complete Protease Inhibitor tablet (Roche) per 25 ml using a Polytron homogenizer (KINEMATICA). The volume of PBS used for homogenization was adjusted to 75 mg of tissue per milliliter of buffer. The homogenate was centrifuged for 15 min at 1,870×g, and the supernatants were centrifuged for 5 min at 13,230×g. The supernatants were subjected to ELISA analysis. ELISA kits of murine IL-1β and IL-6 (BD DuoSet) and mC3a (Bachem) were used according to the protocol of each ELISA kit. C5a was measured by ELISA using a set of specific antibodies to the neo-epitope of C5a-desarg according to manufacturer's protocol (BD). The concentration of total protein in the supernatants was measured using the BCA kit (Pierce). The concentration of cytokines and chemokines was expressed in picograms per milligram of protein.

c. ELISA Analysis

C3a and C5a ELISA's were established using capture and detection antibodies from BD, or using a mouse ELISA kit. Weilisa Total Complement Screen: Protocol was followed per instructions provided by the kit. To access potential CRIg inhibition of the CP, factor B depleted serum was used. To determine CRIg inhibition of the AP, C2 depleted serum was used.

d. Measurement of Cytokine Concentration in Arthritic Hind Paws

Hind footpads of sacrificed mice were cut at the borderline of fur growth and frozen in liquid $N_2$. The footpads were homogenized in ice-cold RIPA lysis buffer supplemented with 1 Complete Protease Inhibitor tablet (Roche) per 25 ml using a Polytron homogenizer (KINEMATICA). The volume of PBS used for homogenization was adjusted to 75 mg of tissue per milliliter of buffer. The homogenate was centrifuged for 15 min at 1,870×g, and the supernatants were centrifuged for 5 min at 13,230×g. The supernatants were subjected to ELISA analysis. ELISA kits of murine IL-1β and IL-6 (BD DuoSet) and mC3a (Bachem) were used according to the protocol of each ELISA kit. C5a was measured by ELISA using a set of specific antibodies to the neo-epitope of C5a-desarg according to manufacturer's protocol (BD). The concentration of total protein in the supernatants was measured using the BCA kit (Pierce). The concentration of cytokines and chemokines was expressed in picograms per milligram of protein.

Results

Figure 4:
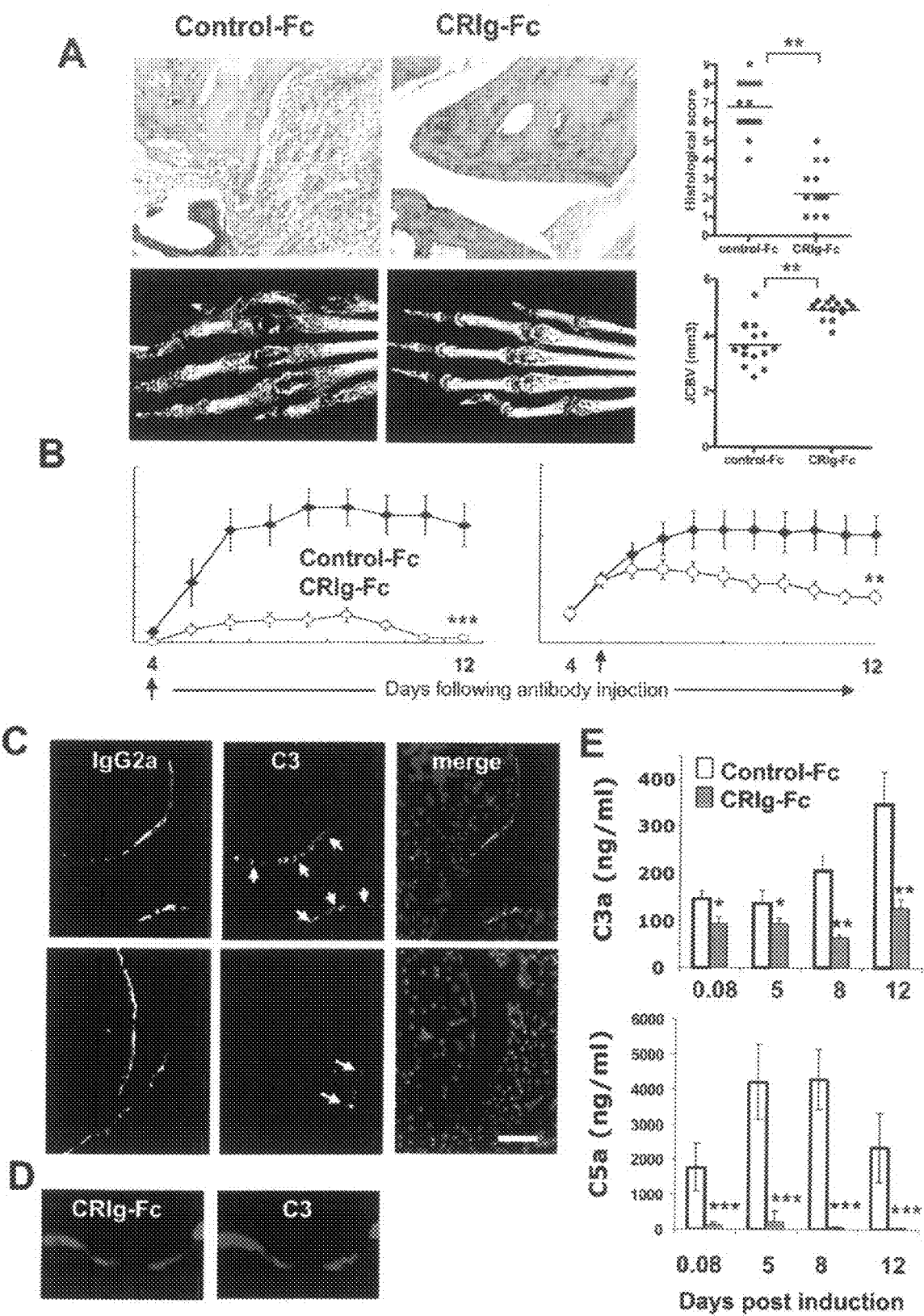
FIG. 4. Systemically administered CRIg-Fc inhibits local and systemic complement activation following antibody-induced arthritis. (A) Reduced inflammation (histology scores) and decreased bone deformation (increased joint cortical bone volume, JCBV) in mice treated with muCRIg-Fc in already established disease, 7 days following secondary immunization with collagen. Metatarsal joints at day 64 were prepared for routine H&E histology, or micro-computed tomography (micro-CT). (B) Reduced clinical scores in mice receiving 3 weekly doses of 12 mg/kg muCRIg-Fc starting 3 days (left panel) or 5 days (right panel) following passive immunization with anti collagen type II antibodies. (C) Treatment with CRIg-Fc inhibits accumulation of C3 fragments, but not IgG2a, on the cartilage surface in the joints. In the merged images, red indicates presence of IgG2a anti collagen antibody, green indicates the presence of complement C3 products on the cartilage surface. (D) Binding of CRIg-Fc (green) on C3 in the joint of a mouse treated with CRIg-Fc in already established disease. Scale bar=20 um. (E) Upper panel: Inhibition of C3a production in the joint in mice treated with CRIg-Fc, starting the day prior to passive immunization. Lower panel: significant reduction of C5a levels in sera of mice treated with CRIg-Fc. Statistical analysis (Student's t-test): * p<0.01,  p<0.001,  p<0.0001.

Soluble regulators of complement activation have proven to be potent therapeutic tools to inhibit complement activation leading to inflammation (H. F. Weisman et al., *Science* 249, 146 (1990); B. P. Morgan, C. L. Harris, *Mol Immunol* 40, 159 (2003)). The therapeutic potential of CRIg was tested in two mouse models of rheumatoid arthritis in which collagen autoantibodies and complement activation contribute to the pathogenesis of the disease (A. Aggarwal, et al., *Rheumatology* (Oxford) 39, 189 (2000); S. Solomon, et al., *Arthritis Res Ther* 7, 129 (2005); K. Terato et al., *J Immunol* 148, 2103 (Apr. 1, 1992)). To extend its pharmacologic half life in vivo the extracellular domain of muCRIg was fused to the Fc portion of mouse IgG1. CRIg significantly reduced joint swelling, histological scores and bone-loss when given before or after clinical signs of arthritis (FIGS. 4A and B, S12). In line with its inhibition of convertase activity, CRIg significantly reduced complement activation in the joint as shown by a decrease of C3 deposition on the cartilage surface (FIG. 4C). In mice with already established disease, CRIg was co-localized with C3 lining the joint (FIG. 4D), indicating that it can bind to and inhibit convertases locally. In addition, local levels of C3a and systemic levels of C5a were significantly lower in CRIg-Fc-treated than in control-Fc-treated mice (FIG. 4E). These results indicate that CRIg inhibits arthritis at the effector phase of the disease by inhibiting local and systemic complement activation. The protective activity of CRIg was independent of Fc receptor function since a mutation in the Fc portion of CRIg-Fc that ablates Fc receptor binding had activity equivalent to CRIg fused to a wt Fc protein (results not shown). Based on these results, the single IgV-like domain of CRIg may serve as a promising protein therapeutic to inhibit the alternative pathway in complement-mediated disorders.

EXAMPLE 5

CRIg Inhibits AP Convertases by Inhibition of Substrate-enzyme Binding

Materials and Methods a. Decay Acceleration Assays

The microtiter plate assay for the alternative pathway DAA was performed as described previously (M. Krych-Goldberg et al., *J Biol Chem* 274, 31160 (1999)). Microtiter plates were coated overnight with 4 µg/ml C3b in phosphate-buffered saline. Plates were blocked for 2 h at 37° C. with phosphate-buffered saline containing 1% bovine serum albumin and incubated for two hours at room temperature with 40 ng of factor B, 10 ng of factor D, and 0.8 mM $NiCl_2$ in veronal buffer containing 71 mM NaCl, 0.05% Tween 20 and 4% BSA (check concentrations and composition of buffer with protocol). Wells were then incubated for 15 minutes at room temperature with factor H or CRIg-His ECD in PBS containing 0.05% Tween 20 (PBST) to dissociate Bb from the C3b on the plate. Bb was then detected with sequential 1 hour incubations with 1:5000 dilution of goat anti-human factor B polyclonal antibody (Kent) in PBST and 1:3000 dilution of donkey anti-goat antibody conjugated to horseradish peroxidase (Caltag) in PBST (check dilutions and secondary antibody with protocol). Color was developed with O-phenylenediamine. In this assay, factor H behaved as expected as mediator of decay accelerating activity.

b. C3b-C4b and C3b-C3b Dimer Preparation and Binding/Competition Assays

Figure 5:
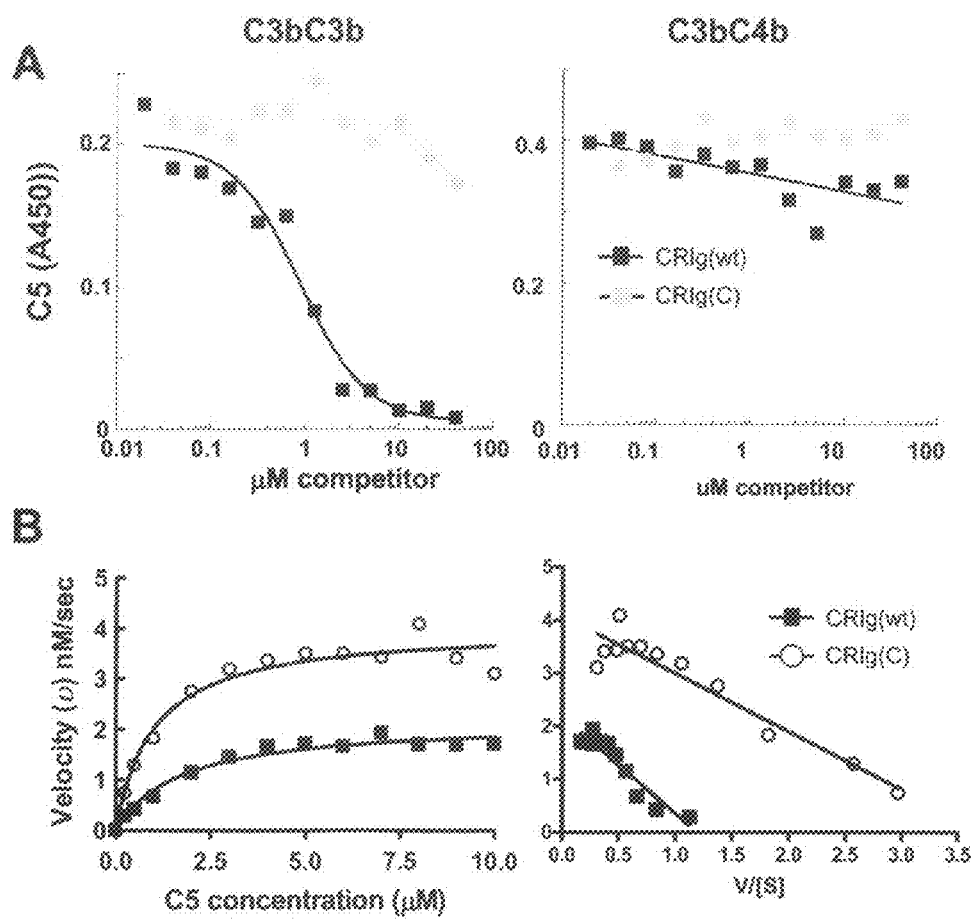
FIG. 5. CRIg inhibits the C5 convertase by inhibiting binding of C5 to the non-catalytic sub-unit of the convertase. (A) CRIg blocks C5 binding to C3b2 but not to C3bC4b. C3b, C3b2 and C3bC4b were captured with a polyclonal anti C3 antibody and incubated with a mixture of C5 with increasing concentrations of CRIg(wt) or mutant CRIg(C). C5 bound to the convertase subunits was detected with a polyclonal anti C5 antibody and a HRPO-conjugated secondary antibody. IC50 for CRIg inhibition of C5 binding was 0.88±0.22 µM. (B) CRIg reduces the Vmax of a purified C5 convertase. A fixed concentration of CRIg was mixed with a zymosan-bound C5 convertase in the presence of increasing concentrations of C5. Km and Vmax values, calculated based on the Michaelis Menten equation, were 0.99 and 4.01 in the absence, and 1.70 and 2.16 in the presence of 0.8 uM CRIg (wt).
Figure 14:
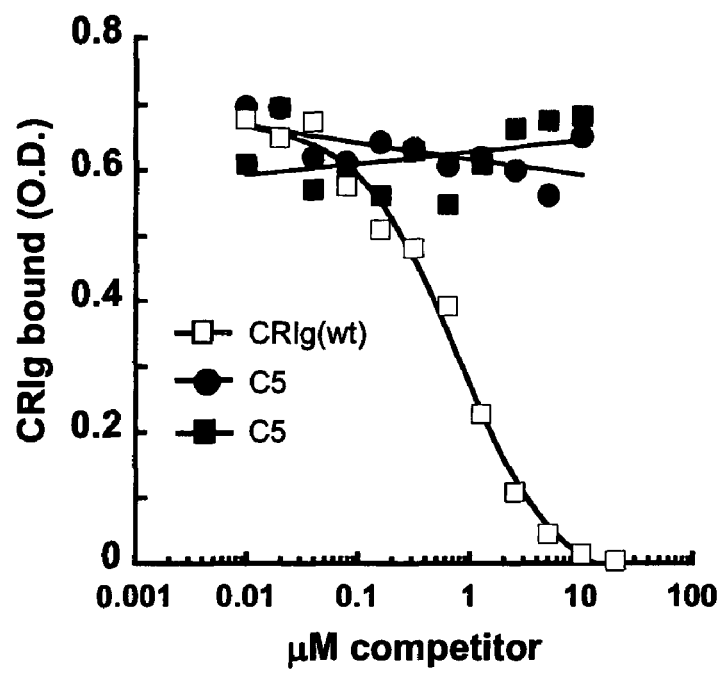
FIG. 14. CRIg ECD, but not C5, can compete with CRIg-LFH binding to C3b. A mixture of CRIg-LFH and increasing concentrations of CRIg-ECD or C5 were added maxisorb plates coated with C3b. The remaining CRIg-LFH bound was detected with a anti flag antibody.

C3bC4b heterodimers were made essentially as described elsewhere (S. Meri, M. K. Pangburn, *Eur J Immunol* 20, 2555 (1990)) with the following modifications (S. Meri, M. K. Pangburn, *Eur. J. Immunol.* 20:2555 (1990)) To determine binding of CRIg to C3b-C4b heterodimer and C3b homodimer, Maxisorp 96-well microtiter plates were coated overnight at 4° C. with 5 ug/ml goat anti-C3 polyclonal antibody (ICN) in PBS and washed 3 times with PBST. Plates were then blocked with 250 µl PBS/1% BSA for 2 hours at room temperature and titrating amounts of hCRIg-L LFH added for 1 hr in PBST containing 1% BSA. Plates were again washed 3 times with PBST and CRIg binding detected with 1:20,000 dilution of mouse anti-FLAG M2 antibody conjugated to HRP (SIGMA) in PBST/1% BSA. Plates were then washed 3 times with PBST and developed with 100 ul TMB substrate solution (KPL) and stopped with 50 ul 2NH2SO4. Absorbance was read at 450 nm. It was also determined that C5 binds to both C3b-C4b heterodimer and C3b homodimer in this format. To determine whether CRIg can block C5 binding to C3b-C4b or C3b-C3b, the complement dimers were captured and blocked as above. Diluted in buffer containing 20 mM TRIS pH 7.5, 20 mM MgCl2, 20 mM CaCl2, 150 mM NaCl, 0.05% Tween 20 and 1% BSA, 400 nM C5 was premixed with titrating concentrations of hCRIg-S His ECD or a mutated version of this fusion that does not bind C3b and added to the captured dimer for 1 hr at room temperature. Wells were then washed 3 times with PBST and C5 was detected by stepwise addition of 1:5000 mouse anti-human C5 (Quidel) and 1:3000 goat F'ab anti-mouse antibody (Caltag) diluted in PBST. The plate was developed as above and the A415 of two wells was averaged and considered a single point Results All known regulators of complement activation serve as co-factors for factor I-mediated cleavage of C3 or are competitors of Bb binding to C3b, thus ablating convertase activity (D. Hourcade, et al., *Adv Immunol* 45, 381 (1989); T. Seya, J. P. Atkinson, *Biochem J* 264, 581 (1989); X. Sun et al., *Proc Natl Acad Sci USA* 96, 628 (1999)). In contrast, CRIg displays neither decay-, nor co-factor-activity. In addition, CRIg does not interfere with the binding of factor H, factor B or properdin to C3b (FIG. S13A-C and results not shown). In order to further explore the mechanism by which CRIg inhibits AP complement activation, we determined whether CRIg interferes with the function of the C3b rather than with the catalytic Bb subunit of the C5 convertase. The non-catalytic C3b subunit of the alternative pathway convertase is responsible for binding of the substrates C3 and C5. The factor Bb subunit of the convertase is then able to act as a protease and cleaves the bound substrate (W. Vogt, et al., *Immunology* 34, 29 (1978)). As a result, the activity of the convertase is directly proportional to the affinity of the substrates to C3b (N. Rawal, M. K. Pangburn, *J Immunol* 164, 1379 (2000)). CRIg prevents C5 binding to the $C3b_2$ subunit of the AP convertase but consistent with its selectivity for the AP C5 convertase (FIG. 5A) has no effect on the C3bC4b subunit of the CP convertase. The consequences of CRIg binding for the activity of the C5 convertase were further determined with the purified C5 convertase (N. Rawal, M. K. Pangburn, *J Biol Chem* 273, 16828 (1998)). In the presence of CRIg, the Vmax of the enzyme was reduced by ~50% (FIG. 5B), indicating that CRIg inhibits the maximal binding capacity of C5 to C3b, independent of substrate concentration. This is indicative of a steric or allosteric inhibition of C5 binding to C3b by CRIg and not of a direct competition of CRIg with C5 for binding to C3b. This is further supported by results from a binding assay in which C5 is not able to compete with CRIg binding to C3b (FIG. 14). Thus, CRIg bound to the center of the key-ring like β-chain structure of C3b can block binding of C5 to the convertase, thus inhibiting the activity of the enzyme. This illustrates the importance of the β-chain of C3b for the interaction of the C5-convertase with its substrate (N. Rawal, M. K. Pangburn, *J Biol Chem* 273, 16828 (1998)).

What is claimed is:

1. A crystal formed by Complement Receptor of the Immunoglobulin superfamily (CRIG) polypeptide having amino acids 1-119 of SEQ ID NO:2 that diffracts x-ray at a resolution of 1.2Å, and has a approximately the following unit cell constants a=30.3 Å, b=50.8 Å, c=62.0 Å, and a space group of $P2_1 2_1 2_1$.

2. A composition comprising a crystal of claim 1.

3. A crystalline form of a complex between Complement Receptor of the Immunoglobulin superfamily (CRIG) having amino acids 1-119 of SEQ ID NO:2 and complement factor C3b that diffracts x-ray at a resolution of 4.1 Å and has approximately the following unit cell constants a=97.6 Å, b=255.7 Å, c=180.3 Å, and a space group of $C222_1$.

4. A crystalline form of a complex between Complement Receptor of the Immunoglobulin superfamily (CRIG) having amino acids 1-119 of SEQ ID NO:2 and complement factor C3c that diffracts x-ray at a resolution of 3.1 Å and has approximately the following unit cell constants a=382.8 Å, b=65.0 Å, c=147.2 Å, β=102.7, and a space group of C2.

* * * * *